United States Patent
Lee et al.

(10) Patent No.: US 9,943,606 B2
(45) Date of Patent: Apr. 17, 2018

(54) DENDRITIC POLYPEPTIDE-BASED NANOCARRIERS FOR THE DELIVERY OF THERAPEUTIC AGENTS

(71) Applicant: Rutgers, The State University of New Jersey, New Brunswick, NJ (US)

(72) Inventors: Ki-Bum Lee, Monmouth Junction, NJ (US); Prasad Subramaniam, Edison, NJ (US); Dipti N. Barman, Carteret, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 273 days.

(21) Appl. No.: 14/594,844

(22) Filed: Jan. 12, 2015

(65) Prior Publication Data

US 2015/0196657 A1  Jul. 16, 2015

Related U.S. Application Data

(60) Provisional application No. 61/927,827, filed on Jan. 15, 2014.

(51) Int. Cl.

| | | |
|---|---|---|
| *A61K 51/00* | (2006.01) | |
| *A61K 36/14* | (2006.01) | |
| *A61K 47/48* | (2006.01) | |
| *A61K 31/704* | (2006.01) | |
| *A61K 38/14* | (2006.01) | |
| *A61K 31/167* | (2006.01) | |
| *A61K 31/337* | (2006.01) | |
| *A61K 31/4745* | (2006.01) | |
| *A61K 31/517* | (2006.01) | |
| *A61K 31/5377* | (2006.01) | |
| *A61K 31/555* | (2006.01) | |
| *A61K 31/713* | (2006.01) | |
| *A61K 47/64* | (2017.01) | |

(52) U.S. Cl.
CPC ...... *A61K 47/48253* (2013.01); *A61K 31/167* (2013.01); *A61K 31/337* (2013.01); *A61K 31/4745* (2013.01); *A61K 31/517* (2013.01); *A61K 31/5377* (2013.01); *A61K 31/555* (2013.01); *A61K 31/704* (2013.01); *A61K 31/713* (2013.01); *A61K 38/14* (2013.01); *A61K 47/641* (2017.08)

(58) Field of Classification Search
CPC .... A61K 49/00; A61K 51/00; A61K 2121/00; A61K 2123/00; A61K 38/00; A61K 47/00; A61K 47/48253; A61K 31/00; A61K 31/185; A61K 31/7088; A61K 31/704; A61K 38/14; A61K 31/167; A61K 31/337; A61K 31/4745; A61K 31/517; A61K 31/5377; A61K 31/555; A61K 31/713; A61K 47/641

USPC .......... 424/1.11, 1.65, 1.69, 1.81, 1.85, 1.89, 424/9.1, 9.2, 9.3, 9.4, 9.5, 9.6; 514/1, 514/1.1, 19.2, 19.3, 19.4, 19.5, 19.6, 21.2, 514/21.3, 21.4, 21.5, 21.6; 530/300, 317, 530/324, 325, 326, 327, 328, 350

See application file for complete search history.

(56) References Cited

U.S. PATENT DOCUMENTS

| | | |
|---|---|---|
| 5,208,020 A | 5/1993 | Chari et al. |
| 5,416,064 A | 5/1995 | Chari et al. |
| 5,475,092 A | 12/1995 | Chari et al. |
| 6,333,410 B1 | 12/2001 | Chari et al. |
| 6,441,163 B1 | 8/2002 | Chari et al. |
| 6,716,821 B2 | 4/2004 | Zhao et al. |
| 6,913,748 B2 | 7/2005 | Widdison |
| 7,276,497 B2 | 10/2007 | Chari et al. |
| 7,276,499 B2 | 10/2007 | Chari et al. |
| 7,368,565 B2 | 5/2008 | Chari et al. |
| 7,388,026 B2 | 6/2008 | Zhao et al. |
| 7,414,073 B2 | 8/2008 | Baloglu et al. |
| 7,989,434 B2 | 8/2011 | Feng |
| 8,012,485 B2 | 9/2011 | Amphlett et al. |
| 8,198,417 B2 | 6/2012 | Steeves et al. |
| 2005/0037417 A1 | 2/2005 | Ruoslahti et al. |
| 2008/0294089 A1* | 11/2008 | Hardy ................. A61K 9/0009 604/22 |

OTHER PUBLICATIONS

Goldmacher et al., " Linker Technology and Impact of Linker Design on ADC Properties," Chapter 7 of "Antibody-drug Conjugates and Immunotoxins: From Pre-clinical Development to Therapeutic Applications," ed. Phillips, GL., Ed. Springer Science and Business Media, New York, 2013 (Abstract only).

Trouet et al., "A covalent linkage between daunorubicin and proteins that is stable in serum and reversible by lysosomal hydrolases, as required for a lysosomotropic drug-carrier conjugate: in vitro and in vivo studies," Proc. Natl Acad Sci USA, 1982, vol. 79, pp. 626-629.

Umemoto et al., "Preparation and in vitro cytotoxicity of a methotrexate-anti-MM46 monoclonal antibody conjugate via an oligopeptide spacer," Int J Cancer, 1989, vol. 43, pp. 677-684 (Abstract only).

* cited by examiner

*Primary Examiner* — D L Jones
(74) *Attorney, Agent, or Firm* — Fox Rothschild LLP

(57) ABSTRACT

Dendritic polypeptides useful for the delivery of therapeutic agents into cells are disclosed, together with their methods of preparation. These dendritic polypeptides serve as carriers of drugs, siRNA, aptamers and plasmid DNA in the treatment of various diseases, including cancer.

22 Claims, 3 Drawing Sheets

SEQUENCE LISTING

```
<160> NUMBER OF SEQ ID NOS: 7

<210> SEQ ID NO 1
<211> LENGTH: 7
<212> TYPE: PRT
<213> ORGANISM: artificial
<220> FEATURE:
<223> OTHER INFORMATION: synthetic targeting peptide

<400> SEQUENCE: 1

Cys Leu Pro Val Ala Ser Cys
1               5

<210> SEQ ID NO 2
<211> LENGTH: 7
<212> TYPE: PRT
<213> ORGANISM: artificial
<220> FEATURE:
<223> OTHER INFORMATION: synthetic targeting peptide

<400> SEQUENCE: 2

Cys Gly Ala Arg Glu Met Cys
1               5

<210> SEQ ID NO 3
<211> LENGTH: 9
<212> TYPE: PRT
<213> ORGANISM: artificial
<220> FEATURE:
<223> OTHER INFORMATION: synthetic targeting peptide

<400> SEQUENCE: 3

Cys Asn Ser Arg Leu His Leu Arg Cys
1               5

<210> SEQ ID NO 4
<211> LENGTH: 9
<212> TYPE: PRT
<213> ORGANISM: artificial
<220> FEATURE:
<223> OTHER INFORMATION: synthetic targeting peptide

<400> SEQUENCE: 4

Cys Glu Asn Trp Trp Gly Asp Val Cys
1               5

<210> SEQ ID NO 5
<211> LENGTH: 21
<212> TYPE: PRT
<213> ORGANISM: artificial
<220> FEATURE:
<223> OTHER INFORMATION: synthetic targeting peptide

<400> SEQUENCE: 5

Trp Arg Cys Val Leu Arg Glu Gly Pro Ala Gly Gly Cys Ala Trp Phe
1               5                   10                  15

Asn Arg His Arg Leu
            20

<210> SEQ ID NO 6
<211> LENGTH: 21
<212> TYPE: RNA
<213> ORGANISM: artificial
<220> FEATURE:
<223> OTHER INFORMATION: synthetic

<400> SEQUENCE: 6
```

```
ggcuacgucc aggagcgcac c                                         21

<210> SEQ ID NO 7
<211> LENGTH: 21
<212> TYPE: RNA
<213> ORGANISM: artificial
<220> FEATURE:
<223> OTHER INFORMATION: synthetic

<400> SEQUENCE: 7
ugcgcuccug gacguagccu u                                         21
```

DENDRITIC POLYPEPTIDE-BASED NANOCARRIERS FOR THE DELIVERY OF THERAPEUTIC AGENTS

CROSS-REFERENCE TO RELATED APPLICATIONS

This application claims priority under 35 U.S.C. § 119(e) to U.S. Provisional Patent Application Ser. No. 61/927,827, filed on Jan. 15, 2014, which is hereby incorporated by reference in its entirety.

STATEMENT REGARDING FEDERALLY SPONSORED RESEARCH OR DEVELOPMENT

This invention was made with government support under Grant No. 1DP2OD006462-01 awarded by the National Institutes of Health, Director's New Innovator Award. The government has certain rights in the invention.

FIELD OF INVENTION

The invention is related to the field of delivery of therapeutic agents for the treatment of diseases, and specifically to the treatment of cancer by the delivery of anticancer drugs and siRNAs to tumor cells using dendritic polypeptide-based nanocarriers.

BACKGROUND OF THE INVENTION

In recent years, significant effort has been devoted to develop nanotechnology-based approaches for drug delivery since it offers a suitable means of delivering small molecular weight drugs, as well as macromolecules such as proteins, peptides or genes by either localized or targeted delivery to the tissue of interest. Several engineered nanomaterials such as dendrimers, liposomes, and metallic nanoparticles have been developed to deliver anticancer drugs to cancer cells. These systems in general can be used to provide targeted (cellular/tissue) delivery of drugs, to improve bioavailability, to sustain the effects of the drug/gene in target tissues, to solubilize drugs, and to improve the stability of therapeutic agents against enzymatic degradation (nucleases and proteases), especially of proteins, peptides and nucleic acids drugs. However, considering the molecular heterogeneity of diseases such as cancer, there continues to be a tremendous interest in the development of drug delivery systems capable of loading and delivering multiple therapeutic agents in order to achieve a synergistic therapeutic effect against aggressive diseases such as brain and breast cancers.

There is a continuing need in the medical arts for new carriers for therapeutic agents, particularly multiple agents, in order to deliver these agents simultaneously in a therapeutically effective dose and in a site-specific manner.

SUMMARY OF THE INVENTION

The dendritic polypeptides of the present invention are uniquely suited to meet these needs.

One aspect of the invention is directed to a dendritic polypeptide nanocarrier. The dendritic polypeptide nanocarrier includes a core atom and three or more arms. Each of the arms independently includes a spacer and a plurality of amino acids. The spacer covalently links the core atom with the plurality of amino acids. The plurality of amino acids comprises a plurality of cysteines, a plurality of lysines, and a plurality of histidines. The plurality of histidines are located at the terminal position of said three or more arms.

In some embodiments, the core atom is nitrogen and the spacer is an optionally substituted $C_{2-8}$ alkyl.

In some embodiments, the dendritic polypeptide nanocarrier has the following formula:

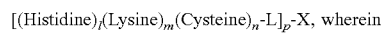

$[(\text{Histidine})_l(\text{Lysine})_m(\text{Cysteine})_n\text{-L}]_p\text{-X}$, wherein l, m, and n are each an integer independently selected from 3, 4, 5, 6, 7, 8, 9, and 10; p is an integer selected from 3, 4, and 5;

X is N, P or C; and

L is a spacer.

In some embodiments of the above formula, l and n are each 3, m is 7, p is 3, and X is N.

Another aspect of the invention is direct to a conjugate comprising the polypeptide dendritic nanocarrier of the present invention and an agent selected from the group consisting of drug, targeting agent, small RNA, sensitizing agent, and diagnostic agent.

In some embodiments, the agent is an anticancer drug selected from taxol, erlotinib, camptothecin, carboplatin, doxorubicin (DOX), paclitaxel, and bleomycin. In some embodiments, the agent of the conjugate is anticancer Doxorubicin (DOX).

In some embodiments, the conjugate further includes a sensitizing agent or a second anticancer drug.

In some embodiments, the sensitizing agent or the second anticancer drug is a histone deacetylase (HDAC) inhibitor or a histone acetyltransferase (HAT) activator, or derivative thereof. In some embodiments, the HDAC inhibitor is suberoylanilide hydroxamic acid (SAHA) or derivative thereof.

In some embodiments, the conjugate further includes a small RNA. In some embodiments, the small RNA is siRNA. In some embodiments, the conjugate further includes a targeting agent.

In some embodiments, the agent in the conjugate is a small RNA. In some embodiments, the small RNA is siRNA. In some embodiments, the conjugate further includes a targeting agent.

Another aspect of the invention is direct to a pharmaceutical composition comprising the conjugate of the present invention and an inert carrier Yet another aspect of the invention is directed to a method of delivering an agent to a target cell, comprising conjugating the agent with the disclosed dendritic polypeptide nanocarrier.

Still another aspect of the invention is directed to a method of treating a disease comprising administering to a subject in need thereof a pharmaceutical composition of the present invention.

Yet another aspect of the invention is directed to a method of diagnosing a disease in a mammal, preferably, human, by administering the pharmaceutical composition of the present invention, wherein the conjugate provides a sufficient amount of an agent to diagnose the disease wherein said agent is a diagnostic agent.

DETAILED DESCRIPTION OF THE INVENTION

Figure 1:
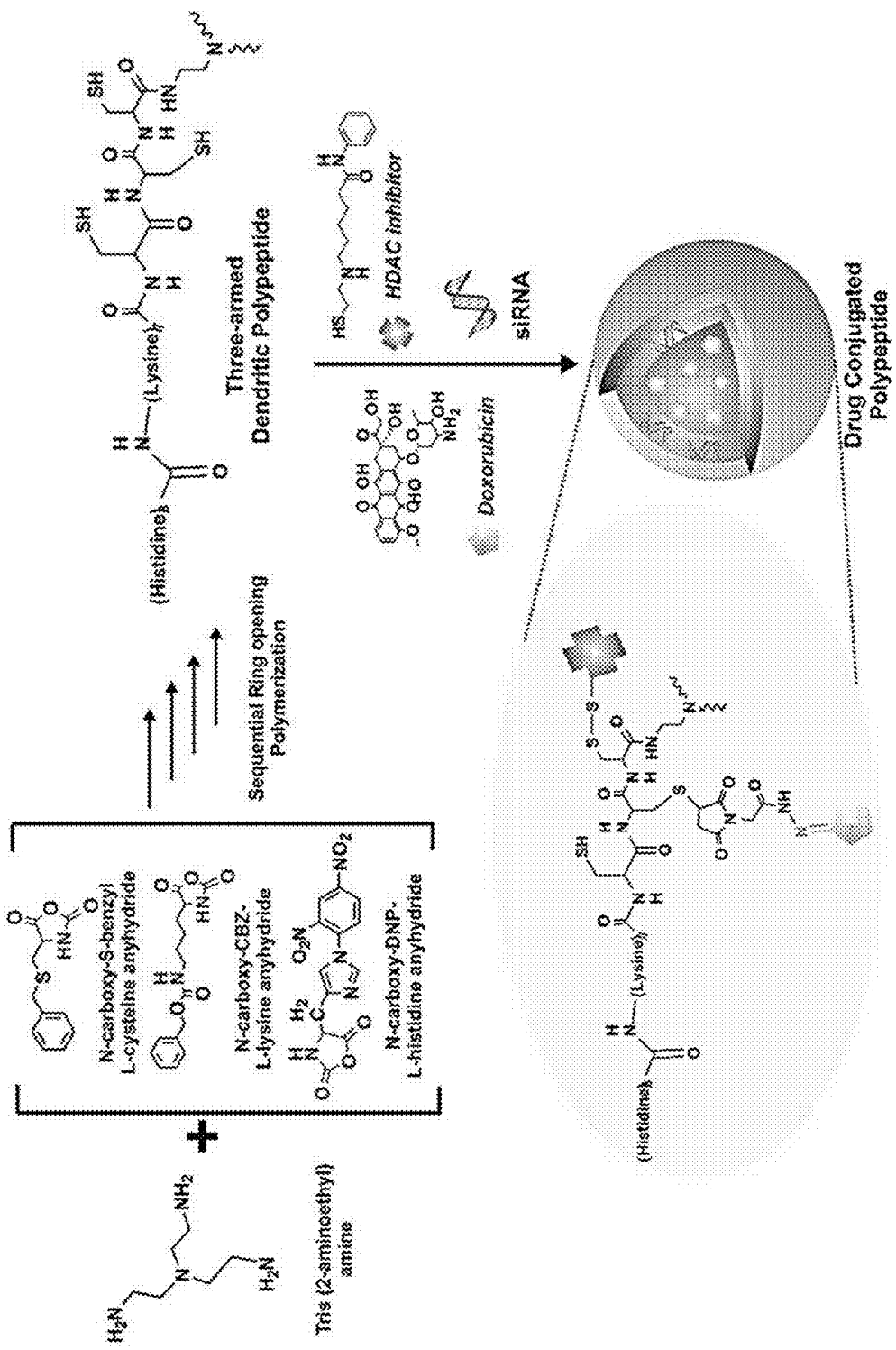
FIG. 1 displays a scheme depicting the synthesis of a dendritic polypeptide of the invention and subsequent conjugation of therapeutic agents to it. The synthesis of the polypeptide backbone was carried out by the sequential ring opening polymerimation using the corresponding amino-acid NCAs and Tris-(aminoethyl) amine as the initiator followed by the conjugation of DOX and HDACi to the cysteine thiol residues using an acid-labile hydrazone linkage and disulfide linkage respectively. The siRNA was complexed to the lysine residues via electrostatic interaction.

It has now been discovered that peptide-based dendrimer systems are amenable for the covalent conjugation of multiple small molecule anticancer drugs and also for the complexation of negatively charged therapeutic small interfering RNA (siRNA). Dendrimers have unique characteristics including monodispersity, modifiable surface functionality, highly defined size and structure with a very high positive surface charge. These attributes allow for the efficient conjugation and delivery of therapeutic agents such as small molecule drugs, siRNA, aptamers and plasmid DNA into cells. In addition, the multivalency of dendritic structures further enhances their interaction with the cellular microenvironment, thereby facilitating drug delivery applications. However, the use of dendrimers is limited by their inherent toxicity; most of the amine-terminated dendrimers bind to negatively charged membranes of cells in a non-specific manner and can cause toxicity in vitro and in vivo. The present invention provides polypeptide-based dendrimers, which are essentially poly-amino acids linked by amide bonds, are biodegradable and biocompatible synthetic polymers with the availability of many side-chain functional groups to conjugate therapeutic molecules. Combing the multivalency of dendrimers with the biocompatibility of polypeptides provides a dendritic polypeptide-based drug delivery platform which enables the conjugation of multiple anticancer drugs and siRNA, and also allows for their efficient delivery to tumor cells in a controlled manner, thereby leading to a synergistic effect. Provided herein is the synthesis of a dendritic polypeptide-based carrier for the controlled delivery of multiple anticancer drugs and siRNA in order to elicit a synergistic inhibition of brain tumor cell proliferation.

While the following text may reference or exemplify specific nanocarriers or conjugates, it is not intended to limit the scope of the invention to such particular reference or examples. Various modifications may be made by those skilled in the art, in view of practical and economic considerations, such as the specific amino acids of the nanocarrier and the agents conjugated to the nanocarrier. All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein. In order to more clearly and concisely describe the subject matter of the claims, the following definitions are intended to provide guidance as to the meaning of terms used herein.

"Conjugate" includes compounds formed via covalent bonding or electrostatic interactions between two chemical entities. Covalent bonding may involve a linker or spacer. A complex can be formed via electrostatic interactions, for example, between lysine residues of a nanocarrier and negatively charged small interfering RNA.

"Agent loading efficiency" is defined as the ratio of the amount of an agent conjugated to the polypeptide nanocarrier to the initial feed amount of the agent used for conjugation.

"Nanocarrier" includes two or more amino acids having one or more functional groups for attaching an agent or complexing to an agent. Each individual amino acid of the nanocarrier backbone can be linked together in tandem or separated by, for example, one or more linkers or non-reactive amino acid spacers. The functional side groups of the amino acids can be reacted with PEGs, or agents or bioactive agents, such as, for example, imaging agents, drugs, radioisotopes, targeting ligands or other peptide monomer backbones. Non-limiting examples of functional amino acids are Lys, which has a primary amino group, Glu or Asp which have a carboxylate group and Cys which has a thiol group. The list of suitable functional amino acids is not limited to those naturally occurring in proteins. For example, diaminobutyric acid having an amino moiety in its side chain can also be used.

"Agent" includes without limitation any diagnostic, therapeutic, palliative, cosmetic and/or prophylactic compositions, including without limitation small molecules, drugs, biologicals, recombinant peptides, proteins and nucleic acids and immunochemicals, as well as diagnostic and imaging compositions, as may be further indicated by the context. In some uses, the term can relate to other types of compositions, as indicated by the context. An agent can be connected either directly on the nanocarrier backbone or through the distal ends of a difunction linker.

"Linkers" include unsubstituted or substituted straight or branched chemical structures, such as those having thiol or other functional groups suitable for attachment of an agent and/or for crosslinking.

"Spacers" provide additional distance between two chemical moieties. Spacers are generally non-cleavable. However, depending on the specific groups at the linkage point and the environmental conditions, the linkage between the spacer and the chemical moiety may be cleavable.

"Therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary.

Dendritic Polypeptide Nanocarrier

One aspect of the invention provides a dendritic polypeptide nanocarrier including a core atom and three or more arms. Each of the arms independently includes a spacer and a plurality of amino acids. The spacer covalently links the core atom with the plurality of amino acids. The plurality of amino acids comprises a plurality of cysteines, a plurality of lysines, and a plurality of histidines. The plurality of histidines are located at the terminal position of the arms. Of course, nanocarriers containing other types of functional atoms such as carbon or phosphorous as the core atom may also be used in the delivery of an agent according to the present invention.

In some embodiments, the core atom is nitrogen and the spacer is an optionally substituted $C_{2-8}$ alkyl. Exemplary alkyl spacers includes a carbon chain having 2, 3, 4, 5, 6, 7, or 8 carbons. The carbon chain can be optionally inserted with one or more heteroatoms such as N, O, and S, or one or more functional groups including for example, amide, ester, and carbamate.

The presence of multiple cysteines and lysines allow for high loading of various agents through covalent bonding or complexing between the agent and the nanocarrier. In some embodiments, each arm of the nanocarrier may independently include 2, 3, 4, 5, 6, 7, 8, 9, 10 or more cysteines or derivatives thereof. In some embodiments, each arm of the nanocarrier may independently include 2, 3, 4, 5, 6, 7, 8, 9, 10 or more lysines or derivatives thereof. In some embodiments, each arm of the nanocarrier may independently include 2, 3, 4, 5, 6, 7, 8, 9, 10 or more histindines or derivatives thereof. In an exemplary embodiments, the dendritic polypeptide nanocarrier of the present invention include 3 or more cysteines or derivatives thereof, 7 or more lysines or derivatives thereof, and 3 or more histidines or derivatives thereof. A derivative of an amino acid may have, for example, a modified functional side chain or a linker or spacer extending from the functional group of the amino acid.

Various components of the nanocarrier can be directly bonded to each other or inter-connected to each other via a linker or spacer. In some embodiments, the cysteins and the core atom are connected via a spacer. In some embodiments, the lysines and the core atom are connected via a spacer. Different types of chemical linkages including for example amide, carbamate, carbonate, ether, disulfide and ester can be utilized at the point of connection. For example, the linkage between the spacer and the cysteine moiety can be an amide. Other types of linkages such as carbamate and ester are also expressly contemplated in the present invention. An additional linker may also be employed between the spacer and the amino acid to allow for control of the degradation of the nanocarrier backbone.

The individual functional amino acids can be bonded to each other in tandem or separated by one or more spacers or linkers. The presence or absence of such spacers or linkers can play an important role including for example modifying the conformation of the peptide monomers, fine tuning the degradation rate of the nanocarrier, or minimizing potential steric hindrance to the agent that the nanocarrier components are designed to interact with.

In some embodiments, a plurality of cysteines may be bonded to each other in tandem. In some embodiments, individual cysteines can be connected to each other via one or more linkers or spacers. In some embodiments, a plurality lysines may be bonded to each other in tandem. In some embodiments, individual lysines can be connected to each other via one or more linkers or spacers. Similarly, individual cysteines at the terminal position of the nanocarrier can be connected to each other directly via one or more linkers or spacers.

In some embodiments, the cysteine section (comprising two or more cysteines) and the lysine section (comprising two or more lysines) are bonded directly via a chemical linkage (e.g. an amide). In some embodiments, the cysteine section and the lysine section may also be connected via a linker or spacer. In some embodiments, the cysteine section of an arm can be inter-woven with the lysine section of the arm. For example, the cysteine section may include one or more lysines, with or without spacers or linkers in between individual amino acids. Likewise, the lysine section may contain one or more cysteines.

Linkers connecting two chemical moieties can be cleavable or non-cleavable. Preparations and applications of linkers are readily available to one of ordinary skill in the art [Goldmacher et al., Antibody-drug Conjugates and Immunotoxins: From Pre-clinical Development to Therapeutic Applications, Chapter 7, in Linker Technology and Impact of Linker Design on ADC properties, Edited by Phillips GL; Ed. Springer Science and Business Media, New York (2013)]. Various linkers are also disclosed in issued U.S. patents (see, for example, U.S. Pat. No. 8,198,417, U.S. Pat. No. 8,012,485, U.S. Pat. No. 7,989,434, U.S. Pat. No. 6,333,410, U.S. Pat. No. 5,416,064, and U.S. Pat. No. 5,208,020). The entire disclosures of the above references are expressly incorporated herein by reference. The linkage connecting a linker with a chemical moiety (e.g. amino acid or agent) includes for example, amide, ester, carbamate, ether, thioether, disulfide, hydrazone, oxime, semicarbazide, and carbodiimide (see for example U.S. Pat. Nos. 5,208,020; 5,475,092; 6,441,163; 6,716,821; 6,913,748; 7,276,497; 7,276,499; 7,368,565; 7,388,026 and 7,414,073). A linker may include one or more functional amino acids.

Cleavable linkers are linkers that can be cleaved under mild conditions. For example, disulfide containing linkers are linkers cleavable through disulfide exchange, which can occur under physiological conditions. Acid-labile linkers are linkers cleavable at acid pH. For example, certain intracellular compartments, such as endosomes and lysosomes, have an acidic pH (pH 4-5), and provide conditions suitable to cleave acid-labile linkers. Linkers that are photo-labile are useful at the body surface and in many body cavities that are accessible to light. Furthermore, infrared light can penetrate tissue. Some linkers can be cleaved by peptidases. Only certain peptides are readily cleaved inside or outside cells, see e.g. Trouet et al., 79 Proc. Natl. Acad. Sci. USA, 626-629

(1982) and Umemoto et al. 43 Int. J. Cancer, 677-684 (1989). Furthermore, peptides are composed of α-amino acids and peptidic bonds, which chemically are amide bonds between the carboxylate of one amino acid and the α-amino group of a second amino acid. Other amide bonds, such as the bond between a carboxylate and the ε-amino group of lysine, are understood not to be peptidic bonds and are considered non-cleavable. Some linkers can be cleaved by esterases. Again only certain esters can be cleaved by esterases present inside or outside cells. Esters are formed by the condensation of a carboxylic acid and an alcohol. Simple esters are esters produced with simple alcohols, such as aliphatic alcohols, and small cyclic and small aromatic alcohols.

Each arm of the dendritic polypeptide nanocarrier can be the same or different. For example, one arm of the nanocarrier may be different from other arms in terms of amino acids, length, linkers, or functional groups. Further, the same amino acid may present itself as different analogs or derivatives in the same arm or different arms. The variations of amino acids, length, or configurations for the nanocarrier arms provide the flexibility of bonding or complexing various agents to the nanocarrier.

In some embodiments, the nanocarrier of the present invention has the following formula: $[(\text{Histidine})_l(\text{Lysine})_m(\text{Cysteine})_n\text{-L}]_p\text{-X}$. X is a core atom of the nanocarrier and can be nitrogen, carbon or phosphorous. L represents is a substituted or unsubstituted spacer linking the core atom with the amino acids. In some embodiments, L is an optionally substituted straight or branched C2-C8 carbon chain, optionally inserted with one or more heteroatoms in the chain. $C_{2-8}$ carbon chains includes a chain with 2, 3, 4, 5, 6, 7, and 8 carbons in the backbone. Heteroatoms that can be optionally inserted into the backbone, in the middle or at the terminal position of the chain, include for example nitrogen, oxygen and sulfur. Various functional groups such as esters and amides can also be inserted in the carbon chain. Each subscript of l, m, and n on each arm is independently 1, 2, 3, 4, 5, 6, 7, 8, 9 or 10. The subscript of p on each arm independently represents an integer of 2, 3, 4, or 5. In some embodiments, X is nitrogen. In some embodiments, l and n are independently selected from 3, 4, 5, 6, 7, or 8. In some embodiments, m is 5, 6, 7, 8, or 9. In some embodiments, L is ethyl, propyl, n-buty, or n-pentyl. For nanocarriers prepared from tris-(2-aminoethyl)amine, L represents a spacer derived from 2-aminoethyl group, X represents nitrogen, and p is 3. The linkage point between the spacer and cysteine is an amide group.

Various synthetic approaches may be employed for the preparation of the nanocarrier of the present invention. For example, the preparation of a nanocarrier may start with a core having a core atom and three or more attached spacers, followed by sequential introduction of amino acids, linkers, spacers, or combinations thereof.

The introduction of amino acids onto each arm of the nanocarrier may entail standard coupling reactions between a carboxylic acid and an amine. Alternatively, as illustrated in the example section of the present invention, the coupling between the N-carboxy anhydride (NCA) of an amino acid and an amine proves to be an efficient and high-yield approach. Various Lewis acids may also be employed to promote the NCA coupling reaction. An added benefit with Lewis acids is the configuration retention of chiral amino acid substrates.

Nanocarrier-Agent Conjugate

Another aspect of the invention provides a polypeptide dendritic nanocarrier-agent conjugate comprising the above described dendritic polypeptide nanocarrier and an agent. The agent is conjugated to one or more of the cysteines or lysines of the nanocarrier.

The agent may be conjugated to one or more (e.g. 1, 2, 3, 4, 5, 6, 7, 8, 9, or 10) cysteines or lysines in one or more arms (e.g. 1, 2, or 3) of the nanocarrier. Any arm of the nanocarrier may independently have 1, 2, 3, 4, or 5 different agents attached thereon. Further, different arms may have different agents attached thereon. Various linkers or linkages as described above can be employed for conjugating an agent to the dendritic polypeptide nanocarrier.

An agent can be conjugated to one or more arms of the polypeptide dendritic nanocarrier. In some embodiments, the agent is a drug and may be selected from the group consisting of anti-inflammatory drugs including: non-steroidal anti-inflammatory drugs (NSAID) and NSAID analogs, indomethacin, sancycline and sancycline analogs, olvanil and olvanil analogs, retro-olvanil and retro-olvanil analogs, olvanil carbamate, NSAID-ache, budesonide and budesonide analogs, methylprednisolone and methylprednisolone analogs and dexamethasone and dexamethasone analogs. Also envisioned is the use of anticancer drugs for conjugation such as camptothecin, carboplatin, doxorubicin (DOX), paclitaxel, bleomycin; anti-HIV drugs including protease inhibitors (non-limiting examples: saquinavir, amprenavir, ritonavir, indinavir, nelfinavir, tipranavir, darunavir and atazanavir) reverse-transcriptase inhibitors, integrase inhibitors viral entry inhibitors (e.g. enfuvirtide) and monoclonal antibodies.

In some embodiments, the agent is an anticancer drug. Non-limiting examples of anticancer drugs include alkylating agents such as thiotepa and cyclosphosphamide (CYTOXAN)™; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolo-melamine; nitrogen mustards such as chlorambucil, chlomaphazine, cholophosphamide, estramustine, ifosfamide, mechlorethamine, mechlorethamine oxide hydrochloride, meiphalan, novembichin, phenesterine, prednimustine, trofosfamide, uracil mustard; nitrosureas such as carmustine, chiorozotocin, fotemustine, lomustine, nimustine, ranimustine; antibiotics such as aclacinomycins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycins, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2'2,"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TOXOTERE™; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (FARESTON™); and anti-androgens such as flutamide, nilutamide, bicalutamide, leuprolide, and goserelin; and pharmaceutically acceptable salts, acids or derivatives of any of the above. In some embodiments, the anticancer drug is DOX.

In some embodiments, the agent is an imaging agent. Suitable non-limiting examples of imaging agents include coloring dyes like FD and C dyes, or visible/near infrared fluorescence dyes like fluorescein, methylene blue, rhodamine, dansyl, Alexa, cyanine dyes, Hilyte, Texas Red, indocyanine green and the like.

In some embodiments, the agent is a cell uptake promoter, transporter, receptor, binding or targeting ligand. Suitable examples of these agents include, without limitations, a vitamin such as, but not limited to, biotin, pantothenate, vitamin B6, or vitamin B12, or analogs thereof. It may also be a carbohydrate for which a transporter exists, such as for glucose and glucose derivatives. It may also be a chemotactic peptide such as a formyl-methionyl peptide. Examples of other peptide targeting agents with a range of size and amino acid order includes the peptide formyl-methionyl-leucyl-phenylalanine (fMLF) peptide and variants thereof which serves as a transport enhancing moiety and increases drug delivery into cells expressing the receptor for that peptide. fMLF is only one example of the class of formyl-methionyl peptides that binds to this receptor. Other examples include other formyl-methionyl peptides and proteins capable of binding to the formyl peptide receptor on the surface of phagocytic cells, which also has been reported to bind to certain other, unrelated peptides lacking the formyl-methionyl moiety, and these latter peptides unrelated to formyl-methionyl peptides but capable of binding to the receptor are fully embraced herein. Other transport enhancing moieties may include Tat-biotin, retro-inverso (RI)-Tat, and RI-TAT-biotin. It may be a chemokine, such as RANTES, SDF-1α, or IL-2. It may also be a peptide such as Tat, penetratin or VEGF, or a membrane fusion peptide such as gp41. It may also be an enzyme such as neuramimidase. It may be an antibody or an antibody fragment with specific affinity for lymphocyte subpopulations, neurons or other cell types. Examples of such antibodies include antibodies to CD4, which may target helper T-cells, or CD44, which may target ovarian cancer cells. It may also be an antigen or epitope such as influenza virus hemagglutinin. It may also be a hormone such as estrogen, progesterone, or growth hormone. It may also be an adhesion molecule such as ICAM, NCAM or a lectin. It may also be a lipid, such as myristic acid or stearic acid. It may be an oligonucleotide or an antisense oligonucleotide such as aptamers containing 5-(1-pentyl)-2'-deoxyuridine. These are merely non-limiting examples. Any of the cell uptake promoters embraced herein may be provided as a form which is capable of being covalently attached to a polymer or therapeutic agent as described above, such as through a functional or reactive group on the cell uptake promoter or by a chemical modification to provide one.

In some embodiments, the agent is a diagnostically useful compound that may be bound via a functional group thereon to the nanocarrier of the invention. Diagnostic moieties having reporter molecules that can be detected by imaging equipment may include radioactive, paramagnetic, fluorescent or radiopaque chemical entities. Specific examples include iodinated sugars that are used as radiopaque agents, and can be appended to linker backbones using ester or other linkages as described above. Additional diagnostic examples include the use of radioactive metal complexes such as Technetium-99m in coordination compounds such as types of, e.g. $^{99m}$Tc-Tetrofosmin or $^{99m}$Tc-Sestamibi, which are used in various types of scintigraphic imaging.

In some embodiments, the agent is an anticancer drug co-existing with a sensitizing agent or a second anticancer drug in the conjugate. Certain sensitizing agents or a second co-existing anticancer drug are able to potentiate the ability of an anticancer drug described above to inhibit cancer-cell growth. Accordingly, the combination of an anticancer drug and a suitable sensitizing agent will produce a synergistic effect when both agents are incorporated into the nanocarrier of the present invention. Specifically, the level of inhibition of cancer-cell proliferation produced by exposing the cells to both the anticancer drug and sensitizer is supraadditive relative to the sum of the inhibitions of cancer-cell proliferation observed by exposing the cells to the anticancer drug alone and to the sensitizer alone.

Various sensitizing agents, which may be an anticancer drug, can be incorporated into the conjugate of the present invention. For example, HDAC inhibitors can act as sensitizing agents for DNA-damaging drugs such as DOX thereby increasing its potency. HDAC inhibitors include compounds of various structural types such as hydroxamic acids, cyclic tetrapeptides, benzamides, electrophilic ketones, and alihpatic acids. Non-limiting examples of HDAC inhibitors include vorinostat (SAHA), belinostat (PXD101), LAQ824, and panobinostat (LBH589); entinostat (MS-275), CI994, mocetinostat (MGCD0103), Vorinostat, Romidepsin, Panobinostat (LBH589), Valproic acid, and Belinostat. The exact dose will depend on the purpose of the treatment, and will be ascertainable by one skilled in the art using known techniques. In some embodiment, the sensitizing agent is SAHA.

Other exemplary embodiments of an anticancer drug co-existing with a sensitizing agent or a second anticancer drug in a conjugate include a topoisomerase II inhibitor (e.g. DOX) with a epigenetic modulators (e.g. HDACi), a topoisomerase I inhibitor (e.g. Camptothecin (CPT)) or other anticancer drug (e.g. taxol, erlotinib) with a epigenetic modulators (e.g. HDACi), a topoisomerase II inhibitor (e.g. DOX) or other anticancer drug (e.g. taxol, erlotinib) with a HAT (histone acetyltransferase) activator, and a topoisomerase I inhibitor (e.g. CPT) with a HAT activator.

Various histone acetyltransferase activators are known in the art, including those disclosed in, for example, U.S. Pat. Application 20130121919.

The ratio between the anticancer drug and the sensitizing agent may vary depending on factors including the specific combination, the type of cancer to be treated, and pharmacological profiles of individual agents. Non-limiting examples of the ratio between the anticancer drug and the sensitizing agent include about 4:1, 3:1, 2:1, 1:1, 1:2, 1:3, 1:4, and 1:5.

In some embodiments, the agent of the conjugate is an anticancer drug and the conjugate further includes a small RNA. Examples of small RNA include RNA molecules of about 18-25 nucleotides in length which can be cleaved out with Dicer, an RNase specific to double-stranded RNA. Small RNA is mainly classified into siRNA (small interfering RNA) and miRNA (microRNA, hereinafter abbreviated as "miRNA"). Small RNAs are known to function as guide molecules for finding target sequences in processes such as translational suppression, mRNA degradation, or alteration of chromatin structure. Small RNAs function via RNA interference (RNAi) or miRNA molecular mechanisms. In addition, small RNAs are also known to play an important role in the regulation of developmental processes (for example, as general remarks, refer to *Jikken Igaku* (Experimental Medicine), 24, pp. 814-819, 2006; and *microRNA Jikken Purotokoru* (microRNA Experimental Protocol), pp. 20-35, 2008, YODOSHA CO., LTD., herein incorporated by reference in their entireties).

The co-existence of an anticancer drug and a siRNA or miRNA in the conjugate of the present invention provides a synergistic anticancer result. Various siRNAs against oncogenes can be incorporated into the conjugate. For example, a siRNA against EGFRvIII oncogene can be co-delivered with an anticancer drug via the nanocarrier of the present invention into the highly invasive U87-EGFRvIII brain tumor cells.

A small RNA can be incorporated to the anticancer drug-containing conjugate, for example, via electrostatic interaction between lysine residues on the nanocarrier arm and the negatively charged RNA. Alternatively, various chemical modifications on the small RNA can be performed to allow for covalent bonding between small RNA and suitable functional amino acids of the nanocarrier. If necessarily, a bifunctional linker as described above can be employed to connect a siRNA with an amino acid of the nanocarrier. Chemical modifications of small RNAs are known in the field for connecting a small RNA to another chemical moiety (see, for example, U.S. Pat. No. 8,779,114). The ratio between the anticancer drug and the small RNA may vary, depending on factors including the specific combination, the type of cancer to be treated, and pharmacological profiles of individual agents. Non-limiting examples of the ratio between the anticancer drug and the small include about 4:1, 3:1, 2:1, 1:1, 1:2, 1:3, 1:4, 1:5, 1:6, and 1:7.

In some embodiments, the conjugate of the present invention further includes a targeting agent. In some embodiments, the targeting agent is a peptide. In some embodiments, the peptide is an RGD peptide. Exemplary targeting peptides include kidney-specific targeting moieties (amino acid sequence CLPVASC (SEQ ID NO: 1) and CGAREMC (SEQ ID NO: 2)) and brain-specific targeting moieties (sequences CNSRLHLRC (SEQ ID NO: 3), CENWWGDVC (SEQ ID NO: 4), WRCVLREGPAGGCAWFN-RHRL (SEQ ID NO: 5)) are brain-specific targeting moieties (see, for example, U.S. Patent Pub. 20050037417). Examples of other peptide targeting agents with a range of size and amino acid order includes the peptide formyl-methionyl-leucyl-phenylalanine (fMLF) peptide and variants thereof which serves as a transport enhancing moiety and increases drug delivery into cells expressing the receptor for that peptide. In some embodiments, an anticancer drug and a targeting agent are both conjugated to the nanocarrier of the present invention.

In order to conjugate various agents to the nanocarrier, chemical modifications of the agent may be required to introduce a particular functional group or a linker. For example, the anticancer drug Dox can be activated with and β-maleimidopropionic hydrazide. The resulting compound then forms a thio-ether linkage with the thiol group of the cysteine in the nanocarrier backbone. An HDAC inhibitor analog can be prepared bearing a terminal thiol group, which reacts with the thiol-containing cysteine to form a di-sulfide linkage.

Another aspect of the invention provides dendritic nanocarrier-RNA conjugate including the above described dendritic polypeptide nanocarrier and a small RNA. In some embodiments, the small RNA is a siRNA. In some embodiments, the small RNA is a miRNA. A small RNA can be complexed to the nanocarrier, for example, via electrostatic interaction between lysine residues on the arm of the nanocarrier and the negatively charged siRNA. Alternatively, various chemical modifications on small RNA can be performed to allow for covalent bonding between the small RNA and suitable functional amino acids of the nanocarrier. If necessarily, a bifunctional linker can be employed to connect a small RNA with an amino acid of the nanocarrier. Various chemical modifications of small RNAs are known in the field for linking a small RNA to another chemical moiety. Any arm of the nanocarrier may be independently complexed to for example 1, 2, 3, 4, 5, 6, 7, 8, 9 or 10, small RNAs.

In some embodiments, the nanocarrier-RNA conjugate further includes any of the above described targeting agent. For example, the targeting peptide Arginyl-glycyl-aspartic acid, having a terminal cysteine residue (RGDC), can be conjugated to the cysteine side chain of the nanocarrier using a disulfide-linkage.

Pharmaceutical Composition

Another aspect of the invention provides a pharmaceutical composition of the above described nanocarrier-RNA conjugate. The pharmaceutical composition further includes one or more inert carrier.

The conjugate of the present invention may be formulated according to methods well known in the art. Briefly, the formulation comprises the conjugate according to any embodiment described above and a pharmaceutically acceptable carrier, as well as any desired excipients. For example, the formulations in the liquid form may comprise physiologically acceptable sterile aqueous or non-aqueous dispersions, suspensions or emulsions and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate.

The conjugate formulations may also contain adjuvants, such as preserving, wetting, emulsifying, and dispersing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of an injectable pharmaceutical form can be brought about by the use of agents delaying absorption, such as aluminum monostearate and gelatin.

Solid dosage forms for oral administration of the conjugate include capsules, tablets, pills, powders, and granules. In such solid dosage forms, the nanocarrier is admixed with at least one of the following: (a) one or more inert excipients (or carrier), such as dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose and *acacia*; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid application forms include emulsions, suspensions, syrups, and elixirs. In addition to the active compounds, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Ultimately, the choice of the formulation depends on the route of administration of the conjugate formulation, which, in turn, may depend on the disease or a condition which is to be treated, prevented or diagnosed.

Method of Delivering an Agent

Another aspect of the invention provides a method of delivering one or more agents to a target cell, comprising forming a conjugate of the agent and the above described dendritic polypeptide nanocarrier. The agent is as described above and includes, for example, anticancer drug, sensitizing agent, small RNA, targeting agent, imaging agent, and diagnostic agent. To form a conjugate, an agent can be bonded directly to the nanocarrier or via a linker as described above. Alternatively, an agent may complex to particular chemical moieties of the nanocarrier via electrostatic interactions to form a conjugate.

One or more agents can be conjugated to each arm of the nanocarrier. An agent may be conjugated independently on each arm of the nanocarrier to 1, 2, 3, 4, 5, 6, 7, 8, 9, or 10 amino acids. Each arm of the nanocarrier may independently include 1, 2, 3, 4, or 5 different agents.

In some embodiments, the conjugate comprises an anticancer drug. In some embodiments, the conjugate comprises DOX. In some embodiments, the conjugate further comprises a sensitizing agent or a small RNA. In some embodiments, the agent is a small RNA. Small RNAs can be siRNA or miRNA Method of Treating a Disease Another aspect of the invention provides a method of treating a disease comprising administering to a subject in need thereof a pharmaceutical composition of the above described conjugate.

In some embodiments, the disease is cancer. In some embodiments, the conjugate comprises an anticancer drug. In some embodiments, the conjugate comprises DOX. In some embodiments, the conjugate further comprises a sensitizing agent or a small RNA. In some embodiments, the conjugate comprises a small RNA. Small RNAs can be siRNA or miRNA.

Depending on the disease or condition, the envisioned administration routes include oral, intravenous, intraarterial, intramuscular, intracolonic, intracranial, intrathecal, intraventricular, intraurethral, intravaginal, sub-cutaneous, intraocular, topical, intranasal, and any combinations thereof.

Method of Diagnosing a Disease

Another aspect of the invention provides a method of diagnosing a disease in a mammal, preferably, human, by administering the above described pharmaceutical compositions, wherein the conjugate of the present invention delivers a diagnostic agent in sufficient amount for diagnosis purposes. The exact amount to be administered depends on the specific disease to be diagnosed, the rout of administration and other relevant factors, and can be ascertained by one of ordinary skill in the art without undue experiments.

EXAMPLES

The synthesis of the dendritic polypeptide was accomplished by the ring opening polymerization of N-carboxy anhydrides (NCAs) using a three-armed amine initiator. The use of NCA chemistry for the ring opening process permits control over the structure of the polypeptide chain by the sequential growth of amino acid monomers from the core. The structure of the three-armed polypeptide was carefully chosen, wherein i) the three cysteine residues per arm were used to conjugate hydrophobic anticancer drugs, thereby increasing their solubility and cellular uptake, ii) the presence of seven lysine residues on each arm allowed for complexing the negatively charged small interfering RNA (siRNA) and also improve the transfection efficiency of the drug conjugates into tumor cells and, iii) the three terminal histidine moieties on each arm facilitated the endosomal escape of the dendritic polypeptide-drug conjugates once taken up by the cancer cells. In addition, targeting moieties such as the cyclic-RGD peptide (cRGD) could be easily attached onto the polypeptide backbone, thereby demonstrating the potential for the targeted delivery of these conjugates. The NCA's of L-lysine, L-cysteine and L-histidine were synthesized according to known methods. The polypeptide backbone was synthesized by the ring opening polymerization (ROP) of the corresponding amino acid NCAs prepared previously using a tri-armed amine as the core initiator, FIG. 1. The control of the molecular weight of dendritic polypeptides via NCA polymerization (in a range less than 5 kD) was achieved by choosing a polar solvent and primary amine (DMF and Tris-(2-aminoethyl)amine respectively).

Materials and Methods

Materials:

N(Σ)-Boc-L-Lysine (98%), L-Histidine (98+%) and Suberic acid (98%) were obtained from Alfa Aesar. S-Benzyl-L-cysteine (97%) was obtained from Sigma Aldrich (St. Louis, Mo.). Tris(2-aminoethyl)amine (96%) was purchased from Acros Organics. Unless otherwise noticed, all solvents were obtained from Fisher Scientific and used as received. The siRNAs targeting the EGFP and EGFRvIII genes were custom designed by Integrated DNA Technologies (Coralville, Iowa). Silencer Cy™-3 labeled Negative Control siRNA was purchased from Invitrogen (Carlsbad, Calif.).

Methods:

The structure and purity of the dendritic polypeptide was confirmed using $^1$H NMR spectroscopy. The molecular weight of the dendritic polypeptide backbone was further confirmed using MALDI-TOF analysis.

Synthesis of HDAC Inhibitor:

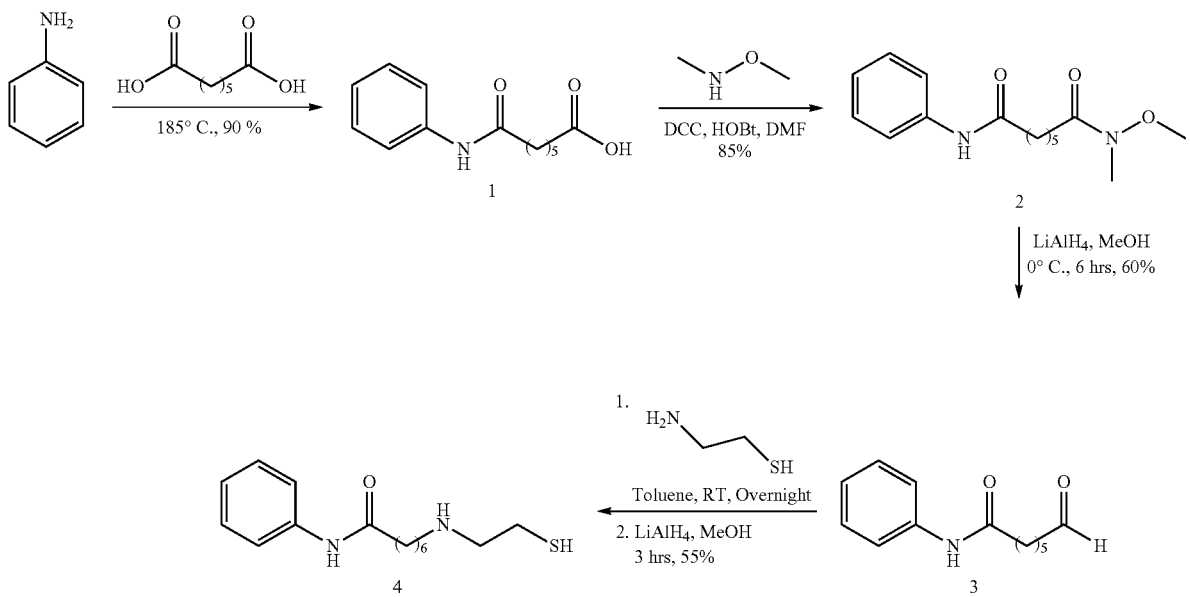

Compound 1:

Commercially available aniline (2 g, 21.47 mM) as reacted with suberic acid (3.8 g, 21.47 mM) at 185° C. for 7 hrs. The resulting solution was cooled to room temperature followed by acid work up to get Compound 1 (70% yield).

Compound 2:

Compound 1 was reacted with DCC and HOBt in dry DMF solution followed by the addition of N,O-dimethyl-hydroxyamidet at room temperature. After 6 hrs of stirring the precipitate was filtered and concentrated in-vacuo to yield compound 2.

Compound 3:

Compound 2 was reacted with LiAlH$_4$ at 0° C. for 3 hrs until the solution became clear. After the completion of the reaction, MeOH was removed in vacuo and then purified using flash chromatography (70:30 Hexane/EtOAc) to yield the product (60% yield).

Compound 4:

Compound 3 was treated with 2-aminoethanethiol in presence of catalytic amount of TsOH. The resulting product was reduced using NaBH$_4$. The final product was puried with flash chromatography in 70:30 EtOAc and Hexane (v/v) to yield the final HDAC inhibitor 4. Yield: 55%. $^1$H NMR (300 MHz, CDCl$_3$), δ 1.63-1.29 (m) 2.85-2.39 (m), 3.02-3.06 (t, J=6.90 Hz), 7.23-7.19 (m), 7.43 (d, J=4.8 Hz). 7.61 (d, J=5.8)

Synthesis of amino acid N-carboxy anhydrides (NCAs)

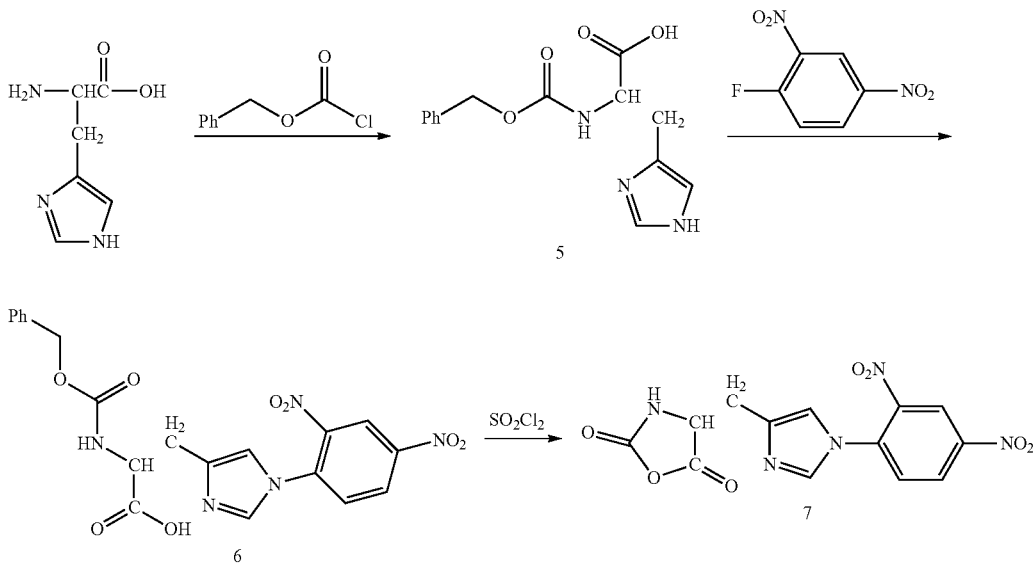

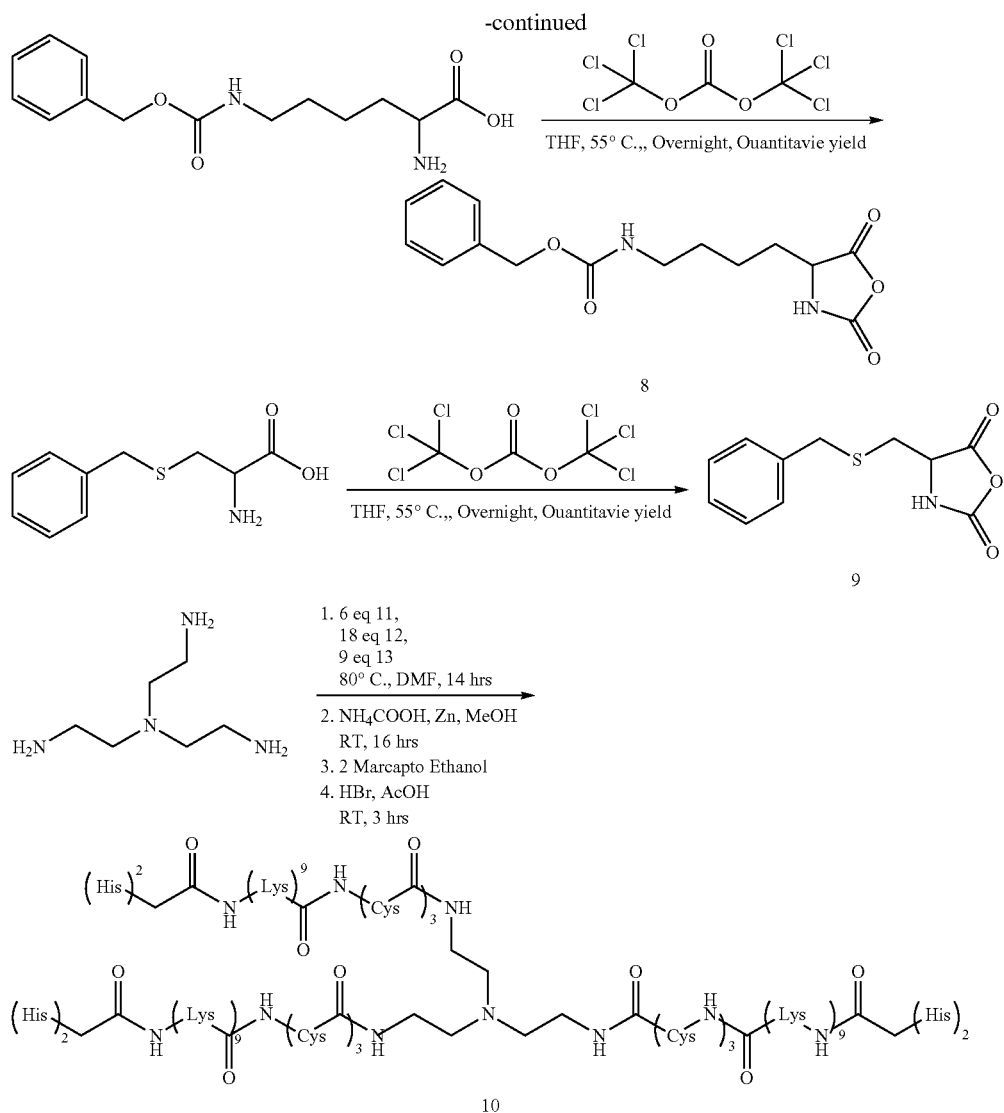

10

Histidine NCA:

N—CBZ-N-DNP-1-histidine (6, 5 g) was dissolved in anhydrous THF (35 ml) and thionyl chloride (0.8 ml) was added. The mixture turned opaque and highly viscous. The reaction was allowed to occur at room temperature, resulting in a clear solution in a few minutes. After another 40 mM, an excess of anhydrous diethyl ether was added to precipitate the product and the precipitate was filtered and dried in vacuo to obtain the product 7. $^1$H NMR (300 MHz, CDCl$_3$), δ 7.86-8.99, 8.05 (d), 7.10 (s), 6.94 (m), 4.52 (m).

Lysine NCA:

CBZ-protected Lys (2.5 g, 8.91 mM) was treated with Triphosgene (1.4 g, 4.45 mM) in dry THF at 0° C. The solution was heated to 45° C. for 12 hrs. Any visible precipitates were removed by filtration and the solvent was removed in vacuo. Recrystallization was carried out with Hexane/THF (1:1; v/v) to yield 8. $^1$H NMR (300 MHz, CDCl$_3$), δ 7.37-7.29 (s, 5H), 5.13 (s, 4H), 4.39-4.3 (d, 2H), 3.6 (s, 2H), 3.23 (s, 2H), 1.9-1.5 (m, 8H)

Cysteine NCA:

S-Benzyl-L-cysteine (2 g, 9.47 mM) was treated with Triphosgene (1.4 g, 4.73 mM) in dry THF at 0° C. The solution was heated to 45° C. for 12 hrs. Any visible precipitates were removed by filtration and the solvent evaporated in vacuo. Recrystallization was carried out with Hexane/THF (1:1; v/v) to yield the product 9. $^1$H NMR (300 MHz, CDCl$_3$), δ 7.38-7.28 (m, 5H), 5.85 (s, 1H), 4.28-4.26 (m, 1H), 3.79 (s, 2H), 3.0-2.79 (m, 2H)

Synthesis of the Dendritic Polypeptide (with and without Histidine)

The dendritic polypeptide was synthesized by the sequential ring opening polymerization (ROP) of the NCAs of L-cysteine, L-lysine, and L-histidine prepared above using Tris(2-aminoethyl)amine as the initiator. 20 µL of Tris(aminoethyl)amine was dissolved in dry DMF and Cysteine-NCA (283 mg, 9 eq) in dry DMF was added to it. The resulting mixture was stirred at 40° C. for 5 hrs and then Lysine-NCA (855 mg, 18 eq) was added. After another 6 hrs, the Histidine-NCA was added to the solution to obtain the protected dendritic polypeptide. The de-protection of the protected cysteine was carried out using reduction in presence of AIBN (1 eq) and $^t$Bu$_3$SnH (2 eq). The removal of the CBZ-group from the Lysine residues was carried out with HBr/AcOH (stirred for 2 hrs at room temperature) to yield the dendritic polypeptide 10. The final product further purified using dialysis (~3000 MWCO) and characterized using NMR and MALDI-TOF analysis. ¹H NMR (300 MHz, CDCl₃), δ 8.06 (s, 1H), 5.3 (s, 10H), 4.89 (m, 6H), 5.2-4.98 (m, 12H), 3.6-3.2 (m, 6H), 2.7-2.56 (m, 12H), 1.58-1.2 (m, 38H). The average molecular weight of the dendritic polypeptide was found to be 4931 daltons, which was very close to the calculated weight of 4922 daltons. Collectively, these results prove the efficiency of the NCA-based synthetic method for obtaining the dendritic polypeptide with the desired amino acid sequence.

Another dendritic polypeptide without the histidine was synthesized using the above method by just excluding the use of Histidine-NCA.

Conjugation of DOX and HDAci to the Dendritic Polypeptide:

dopropionic hydrazide (BMPH, Pierce, Rockford, Ill.). DOX (62 mg, 1 eq) and BMPH, (34 mg, 1 eq) were dissolved in 5 mL anhydrous methanol in presence of 20 μL of TFA. The reactants were stirred for 16 hrs at 20° C. in the dark and concentrated in-vacuo. This activated-Dox (2 eq) was used in a second reaction with the dendritic Polypeptide-HDACi (1 eq) in HEPES buffer (0.1 M NaH₂PO₄, 1 mM EDTA, pH=7.0). Excess DOX was removed from the solution by centrifugal filtration and subsequent dialysis (3000 MWCO) against PBS buffer. The attached DOX was confirmed using NMR and UV visible spectroscopy.

Instrumentation.

The dendritic polypeptides were characterized by NMR and the molecular weight was determined by MALDI-TOF analysis. ¹H and ¹³C NMR spectra were recorded at 500 MHz Bruker instrument. NMR chemical shifts were

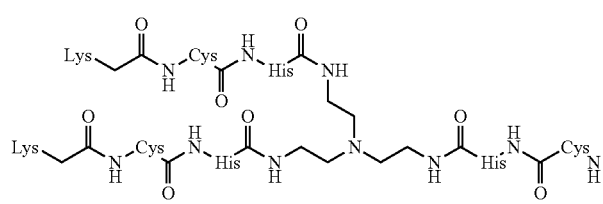

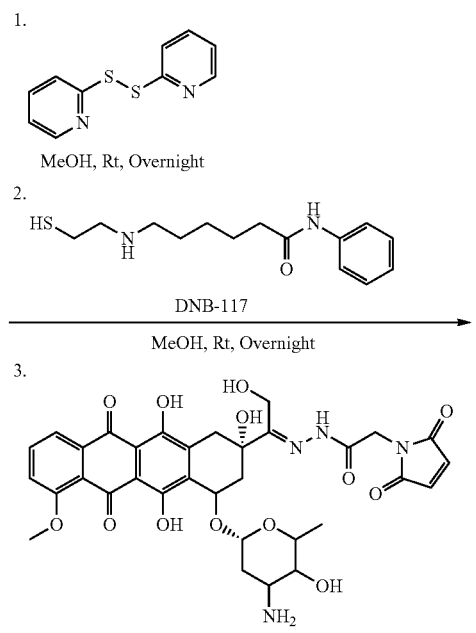

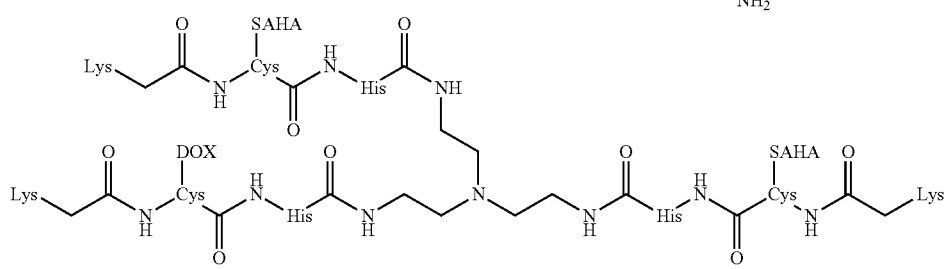

Activation of HDACi and Conjugation to Dendritic Polypeptide:

Disulfide linkage of compound 4 and compound 10 were done in room temperature and in MeOH. Compound 4 (2 eq) and 2,2'-Bipyridyl disulfide (2 eq) were dissolved in MeOH and stirred at room temperature for 24 hrs. After extraction with the EtOAc and water, the unreacted compound could be removed and the attached HDACi was confirmed by NMR.

Activation of DOX and Subsequent Conjugation to Dendritic Polypeptide:

Commercially available Doxorubicin (DOX, LC Laboratories, Woburn, Mass.) was activated with and β-maleimireported as values in ppm relative to deuterated solvents D₂O (4.80). The size and zeta potential were measured using Zetasizer (NanoZS) dynamic light scattering instrument (Malvern Instruments, Malvern, UK). Cellular imaging studies were carried out using a Nikon Ti-Eclipsed 2000 Epifluorescence microscope (Nikon Inc.). HDAC inhibition and cell viability assays were carried out using a Tecan microplate Reader (Tecan Instruments).

MALDI-TOF Analysis:

The molecular weight of the synthesized dendritic polypeptide was determined using matrix-assisted laser desorption ionization-time of flight (MALDI-TOF) mass spectroscopy analysis. The dendritic polypeptide (1.0 mg/mL) was mixed with α-Cyano-4-hydroxycinnamic acid (CHCA, 2.5 mg/mL) as the matrix in 50% ACN/0.1% TFA and spotted onto a MALDI plate. The spots were then analyzed using TOF ABI-4800 mid mass positive-reflector mode.

DLS and Zeta Potential Measurements:

The size and zeta potential of the dendritic polypeptide and dendritic polypeptide-DOX-HDACi drug conjugates were measured at 633 nm using Zetasizer (NanoZS) dynamic light scattering instrument (Malvern Instruments, Malvern, UK) at 25° C. with detection angle of 90°. The dendritic Polypeptide and dendritic Polypeptide-drug conjugates were diluted in phosphate buffered saline (PBS, pH=7.4) and then subjected to DLS and Zeta-potential measurements. At least three measurements were taken for each sample and the mean values were reported.

Loading Efficiency of DOX and HDACi onto Dendritic Polypeptide:

Loading efficiency was defined as the ratio of the amount of DOX or HDACi conjugated to the dendritic polypeptide to the initial feed amount of the drug used for conjugation. Briefly, a solution of DOX-loaded dendritic polypeptide (30.0 µg/mL) in phosphate buffered saline (PBS, pH=7.4) was taken and the absorbance of solution was measured at 494 nm using a Cary Eclipse UV-visible spectrophotometer (Varian, USA). The amount of DOX conjugated to the dendritic polypeptide was then determined from a standard curve of DOX's absorbance at 494 nm versus the concentration. The concentration was then converted to mass of DOX on dendritic polypeptide and the loading efficiency of DOX was then calculated using the theoretical feed amount of DOX (14.68 µg of DOX) corresponding to the amount of dendritic polypeptide used. It was further confirmed using $^1$H NMR integration The amount of the HDACi conjugated on the dendritic polypeptide was determined using NMR integration of a solution of the HDACi-dendritic polypeptide (2.0 mg/mL in CDCl$_3$), which showed that 1.5 molecules of HDACi were present on each dendritic polypeptide. The loading efficiency of the HDACi was then calculated using the theoretical feed amount of HDACi used in a reaction corresponding to the weight of dendritic polypeptide used.

pH-Mediated DOX Release from Dendritic Polypeptide:

The DOX-loaded dendritic polypeptide (30 µg) was taken in microcentrifuge tubes and suspended in PBS buffer maintained at different pH (pH=7.4 and pH=6.0) over a period of 48 hours. At various time intervals, the solutions were centrifuged using a membrane-based filter (3000 MWCO, Amicon, Millipore) in order to assay the amount of DOX released. The percentage of drug released at any given time was directly calculated from the measured absorbance of the free DOX at 494 nm and comparison to a DOX standard calibration curve.

Glutathione-Mediated HDACi Release from Dendritic Polypeptide:

Solutions of HDACi-dendritic polypeptide (1.0 mM) in PBS (pH=7.4) were taken in microcentrifuge tubes. Glutathione (GSH, Sigma Aldrich) was then added to them to obtain final concentrations of 1, 2, 3, 4, and 5 mM of GSH and incubated for 30 minutes to allow for the reductive cleavage of the HDACi from the dendritic polypeptide. The solutions were then loaded onto a LC-MS instrument (LC-10, Shimadzu Scientific Instruments; Columbia, Md.) having an Agilent ZORBAX C-18 column (SB-C18, 3.5 µm, 4.6×75 mm) and eluted with an isocratic flow of 1.0 mL min$^{-1}$ of water:Methanol:TFA [90:10:0.01]. The HPLC data was quantified by the integrated area under the peak at 4.2 mins (elution time of free HDACi as determined using calibration curve) and used to quantify the drug release. It should be noted that the peak at 4.2 mins corresponded to a molecular weight of 267.6, which in turn matched the molecular weight of free HDAC. The amount and the percentage of the HDACi released at various GSH concentrations was then calculated from a calibration curve of the HDACi obtained by running solutions of the HDACi only (in methanol) of various concentration (0, 2, 3, 4, 5 and 10 mM) on the LC-MS and the monitoring the peak area at 4.2 mins.

Culture of Human U87 Glioblastoma Cells and HeLa Cells:

The EGFRvIII overexpressed U87 glioblastoma cells (U87-EGFRvIII) and human cervical cancer cells (HeLa) were cultured using previously reported methods. For U87-EGFRvIII cells, DMEM with high glucose, 10% fetal bovine serum (FBS, Gemini Bioproducts), 1% Streptomycin-penicillin and 1% Glutamax (Invitrogen, Carlsbad, Calif.) were used as basic components of growth media including Hygromycin (100 µg/ml, Life Technologies, Carlsbad, Calif.) as a selection marker. For the HeLa cells, DMEM (with high glucose) supplemented with 10% fetal calf serum (FCS, Gemini Bioproducts), 1% Streptomycin-penicillin and 1% Glutamax was used as the growth medium. All cells were maintained at 37° C. in humidified 5% $CO_2$ atmosphere.

Assessment of Cytotoxicity of HDACi and DOX in DMSO

U87-EGFRvIII cells were grown to 40-60% confluency in a 48-well plate. DOX and HDACi dissolved in DMSO were added to the cells at various concentrations using serial dilution so as to keep the total DMSO concentration at 0.1%. Cells treated with just DMSO were treated as control. The cells were washed with PBS (pH-7.4) after 6 hours and fresh growth media was added. The transfected cells were allowed to grow for 48 h, after which the cell viability was assessed using the CellTiter 96 AQueous One Solution Cell Proliferation Assay (MTS assay, Promega, Madison, USA) according to the manufacturer's recommended protocol.

Assessment of HDAC Inhibition Capability of Synthesized HDACi:

U87-EGFRvIII cells were grown to 40-60% confluency in a 100 mm dish. The cells were then treated with 2.0 mM of HDACi in DMSO. Cells treated with only dendritic polypeptide and DMSO were used as controls. The final DMSO concentration was kept below 0.1% in order to avoid any cytotoxicity. The cells were washed with PBS (pH=7.4) after 6 hours of transfection and fresh growth media was added. The transfected cells were allowed to grow for 48 h, after which the extent of HDAC inhibition was determined using an HDAC Fluorometric immunoassay kit (Cayman Chemical Company, MI, USA) using the manufacturer's recommended protocol Assessment of Cytotoxicity of Dendritic Polypeptide-Drug Conjugates:

U87-EGFRvIII cells were grown to 40-60% confluency in a 48-well plate. The dendritic polypeptide-drug conjugates (dendritic Polypeptide-DOX, dendritic Polypeptide-HDACi, dendritic Polypeptide DOX+dendritic Polypeptide-HDACi and dendritic Polypeptide-DOX-HDACi) were suspended in PBS (pH=7.4) and diluted using Opti-MEM (Invitrogen, Carlsbad, Calif.) to the required concentrations. The conjugates were added to the cells. Cells treated with only dendritic polypeptide was used as the control. The cells were washed with PBS (pH-7.4) after 6 hours of transfection and fresh growth media was added. The transfected cells were allowed to grow for 48 h, after which the cell viability was assessed using the CellTiter 96 AQueous One Solution Cell Proliferation Assay (MTS assay, Promega, Madison, USA) according to the manufacturer's recommended protocol.

Assessment of siRNA Uptake and Targeted Delivery of Dendritic Polypeptide-RGD-siRNA:

Firstly, the uptake and efficient release of siRNA into U87-EGFRvIII cells was assessed by complexing the dendritic polypeptide (with or without histidine moeities) with Silencer Cy™-3 labeled Negative Control siRNA at an N/P ratio of 10 using Opti-MEM media. U87-EGFRvIII cells were grown to 40-60% confluency in a 24-well plate and the dendritic polypeptide-siRNA conjugates were added to them. After 6 h of transfection, the cells were washed and media exchanged with fresh growth medium. The cells were then grown for 24 hours after which the cells were imaged using fluorescence microscopy (Nikon Ti-Eclipsed Inverted Fluorescence microscope, Nikon Instruments, USA). Each image was captured with different channels and focus. Images were processed and overlapped using the NIS-Elements software (Nikon, USA). For the targeted delivery of siRNA, cysteine-terminate RGD peptide (RGDC, 50 nmol, American Peptides, USA) was mixed with the histidine dendritic polypeptide (50 nmol) in PBS (pH=7.4) and allowed to stir for 3 hours at room temperature. The unconjugated RGDC peptide was then removed using centrifugal filtration (3000 MWCO, Millipore). The RGD-conjugated dendritic polypeptide was then complexed with the Silencer Cy™-3 labeled Negative Control siRNA at an N/P ration=10. For the targeting experiments, U87-EGFRvIII and HeLa cells were grown to 40-60% confluency in a 24-well plate and the RGD-dendritic polypeptide-siRNA conjugates were added to them. Cells treated with only dendritic polypeptide-siRNA (without RGDC peptide) were used as controls. All transfection were performed in Opti-MEM media. After 4 h of transfection, the cells were washed and media exchanged with fresh growth medium. The cells were then grown for 24 hours after which the cells were imaged using fluorescence microscopy (Nikon Ti-Eclipsed Inverted Fluorescence microscope, Nikon Instruments, USA). Each image was captured with different channels and focus. Images were processed and overlapped using the NIS-Elements software (Nikon, USA).

Assessment of GFP Knockdown Using Dendritic Polypeptide-siEGFP:

The EGFP overexpressed U87 glioblastoma cells (U87-EGFP) were cultured using DMEM with high glucose, 10% fetal bovine serum (FBS, Gemini Bioproducts), 1% Streptomycin-penicillin and 1% Glutamax (Invitrogen, Carlsbad, Calif.). Geneticin G418 (100 µg/ml, Invitrogen) was used as a selection marker for the U87-EGFP cells. All cells were maintained at 37° C. in humidified 5% CO2 atmosphere. For the knockdown experiments, cells were grown to 40-60% confluency in a 24-well plate. The dendritic Polypeptide (0.2 mg/mL) was complexed with 50 pmol siRNA against EGFP (siGFP) at an N/P (nitrogen to phosphate ratio) of 10. The siRNA for EGFP was designed as follows; Sense sequence was 5'-GGCUACGUCCAGGAGCGC ACC (SEQ ID NO: 6) and Antisense sequence was 5'-phosphate-UGCGCUC-CUGGACGUAGCCUU (SEQ ID NO: 7). The dendritic polypeptide-siGFP conjugates were dispersed in the transfection media (Opti-MEM) and added to the U87-EGFP cells. U87-EGFP cells treated with dendritic Polypeptide-scrambled siRNA were used as a control. After 6 hours of incubation, the solution in each well was removed and exchanged with the growth medium. The cells were allowed to grow for 72 hours after which the GFP knockdown was quantified using fluorescence microscopy (Nikon Ti-Eclipsed Inverted Fluorescence microscope, Nikon Instruments, USA). Each image was captured with different channels and focus. Images were processed and overlapped using the NIS-Elements software (Nikon, USA).

Delivery of Dendritic Polypeptide-DOX-siEGFRvIII:

Dendritic Polypeptide-DOX-siEGFRvIII conjugates were dispersed in the transfection media (Opti-MEM) to get a siRNA concentration of 150 nM and DOX concentrations of 1 and 5 µM. The conjugates were added to the U87-EGFRvIII cells grown to 40-60% confluency in a 48-well plate. Cells treated with dendritic Polypeptide-scrambled siRNA were used as a control. After 6 hours of incubation, the solution in each well was removed and exchanged with the growth medium. The cells were allowed to grow for 48 hours after which the extent of cell proliferation was assessed using the CellTiter 96 Aqueous One Cell proliferation assay kit (Promega, Madison, Wis.). Experiments were carried out in triplicates and the cell viabilities reported as the means±SE.

The dendritic polypeptide carrier preferably contains cysteine residues for small molecule drug conjugation, lysine residues for cellular translocation, and histidine residues for endosomal escape. These residues also confer desirable aqueous solubility. Conjugation of multiple anticancer drugs onto the dendritic polypeptide can be accomplished in a facile manner. Doxorubicin (DOX) and a histone deacetylase inhibitor (HDACi) were selected as model drugs for demonstrating one embodiment. DOX is a widely used chemotherapeutic for the treatment of several aggressive cancers such as head and neck carcinoma, melanoma, brain, breast, ovarian and liver cancer. DOX is known to induce cellular toxicity by the inhibition of topoisomerase II, an enzyme responsible for DNA replication. However, the toxic dose-limiting side effects of DOX, such as cardiotoxicity and nephrotoxicity, result in a narrow therapeutic index. In addition, aggressive tumors such as brain and breast tumors display multiple modes of drug resistance to DOX and other chemotherapeutics, which further limit its therapeutic efficacy. In this regard, the use of HDAC inhibitors, agents which modulate the histone decondensation and hence enhance the unpacking of the chromatin, have emerged as promising candidates for the treatment of cancers. Thus, HDAC inhibitors can act as sensitizing agents for DNA-damaging drugs such as DOX thereby increasing its potency. It has been reported that the co-delivery of DOX and the FDA-approved HDAC inhibitor, suberoylanilide hydroxamic acid (SAHA), potentiated the anticancer activity of DOX in glioblastoma and breast cancer cell lines. It was found that the increased efficacy was due to the increase in the expression level of p53, which is a key tumor suppressor gene, often found in lower levels in brain and breast cancers. Several limitations were apparent which need to be overcome in order to achieve efficacy in a clinical setting. The low aqueous solubility of these traditional HDAC inhibitors requires the use of solvents such as DMSO for their delivery, which severely limits their therapeutic efficacy in vivo. Additionally, the delivery of these drugs would require their release in a controlled manner inside the cells in order to overcome dose limiting toxicities of the anticancer drugs. The dendritic polypeptides of the present invention provide a solution to these problems.

Thus, use of an inventive dendritic polypeptide as a delivery vehicle helps in solubilizing these hydrophobic drugs, thereby increasing their uptake and leading to a corresponding increase in their potency. In addition, the inventive dendritic polypeptide also provides a suitable handle for controlling release of the drugs inside the cells by physical and/or chemical stimuli (HDACi using reducible disulfide bond and DOX via acid-cleavable hydrazone linkage). The dendritic polypeptide also aids in the complexation of siRNA against specific oncogenes, which could be used in conjunction with the drugs to further enhance their efficacy. Furthermore, the use of the inventive dendritic polypeptide helps in achieving higher drug loading efficiencies as compared to traditional drug delivery systems such as liposomes and self-assembling chimeric polypeptides. Towards this end, a non-hydroxamate thiol-based SAHA analogue (henceforth referred to as HDACi) was synthesized in order to attach it onto the dendritic polypeptide carrier using a disulfide linkage. The synthesis of the HDACi was achieved as described in the Examples, vide infra. Doxorubicin was activated by reacting it with β-malemidopropionic hydrazide (BMPH). Activated DOX was immediately used in a second reaction with the dendritic polypeptide (2:1 mole ratio DOX:dendritic polypeptide). Following this, the HDACi was attached to the cysteine —SH of the DOX-conjugated dendritic polypeptide using a disulfide linkage, FIG. 1.

The hydrodynamic sizes and polydispersity indices (PDI) of the dendritic polypeptide-backbone and the drug-conjugated dendritic polypeptide were analyzed using dynamic light scattering (DLS). It was found that the dendritic polypeptide backbone itself had an average size of ~68 nm (PDI=0.138), which increased to 95 nm (PDI=0.3) after drug conjugation. The small increase in size can be attributed to the steric repulsions due to the conjugation of the drugs. However, this size is optimum for escaping renal clearance while having sufficient cell uptake via endocytosis. The zeta potential of the dendritic polypeptide was also measured, both before and after the conjugation of the drugs. The dendritic polypeptide backbone, owing to the large number of lysine residues, was found to have a high positive charge (as evidenced by the positive zeta potential of 26.0 mV). In addition, there was no appreciable change in the zeta potential after drug conjugation (23.1 mV), which would later facilitate the efficient complexation of siRNA for co-delivery to cancer cells. The drug loading efficiencies of DOX and HDACi on the dendritic polypeptide were characterized using UV-visible spectroscopy and LC-MS respectively. A drug loading efficiency of 94% for DOX and 80% for the HDACi was achieved, which is remarkably higher compared to those reported in literature (~20%). This could be attributed to the covalent conjugation of the drugs as opposed to their hydrophobic encapsulation using the self-assembly process often used in the traditional liposomal and polymer-based formulations. Thus, higher drug amounts per unit weight of the polypeptide could be loaded, which is extremely beneficial for in vivo applications. Having characterized the physical properties of the dendritic polypeptide-drug conjugates, their capability to release the conjugated drugs inside the cells in a controlled manner was examined. The release of drug moieties from the dendritic polypeptide backbone requires the pH-dependent cleavage of the hydrazone bond (in case of DOX) and the redox-dependent cleavage of the disulfide bond (in case of HDACi). To verify the kinetics of DOX release, the drug-conjugated dendritic polypeptide was incubated at pH=7.4 and pH=6.0 at 37° C. for 48 h. The fraction of the DOX released over a period of 48 hours was determined by monitoring the absorbance peak at 495 nm using UV-Visible spectroscopy. At pH 7.4, the hydrazone bond was stable, with only minimal DOX release (22%) over a period of 48 hours. On the other hand, at pH 6.0, free DOX was gradually released and reached a maximum amount of 75.4% of the initial amount of DOX, which was similar to the levels observed with other polymeric hydrazones. In a similar fashion, the release of the HDACi was determined by incubating the drug-conjugated dendritic polypeptide with increasing concentrations of glutathione (GSH) and monitoring its release using LC-MS. GSH is an enzyme found inside cells which mediates the cleavage of disulfide bonds of cellular proteins. It was found that the release of the HDACi increased as the concentration of GSH was increased from 0 to 5 mM, with a maximum release of 40% within 30 minutes of incubation in 5 mM GSH. These observations confirm that the dendritic polypeptide-drug conjugates are extremely stable at physiological conditions, while being released inside cells in a controlled manner when in contact with appropriate stimuli (acidic pH and GSH).

Figure 2:
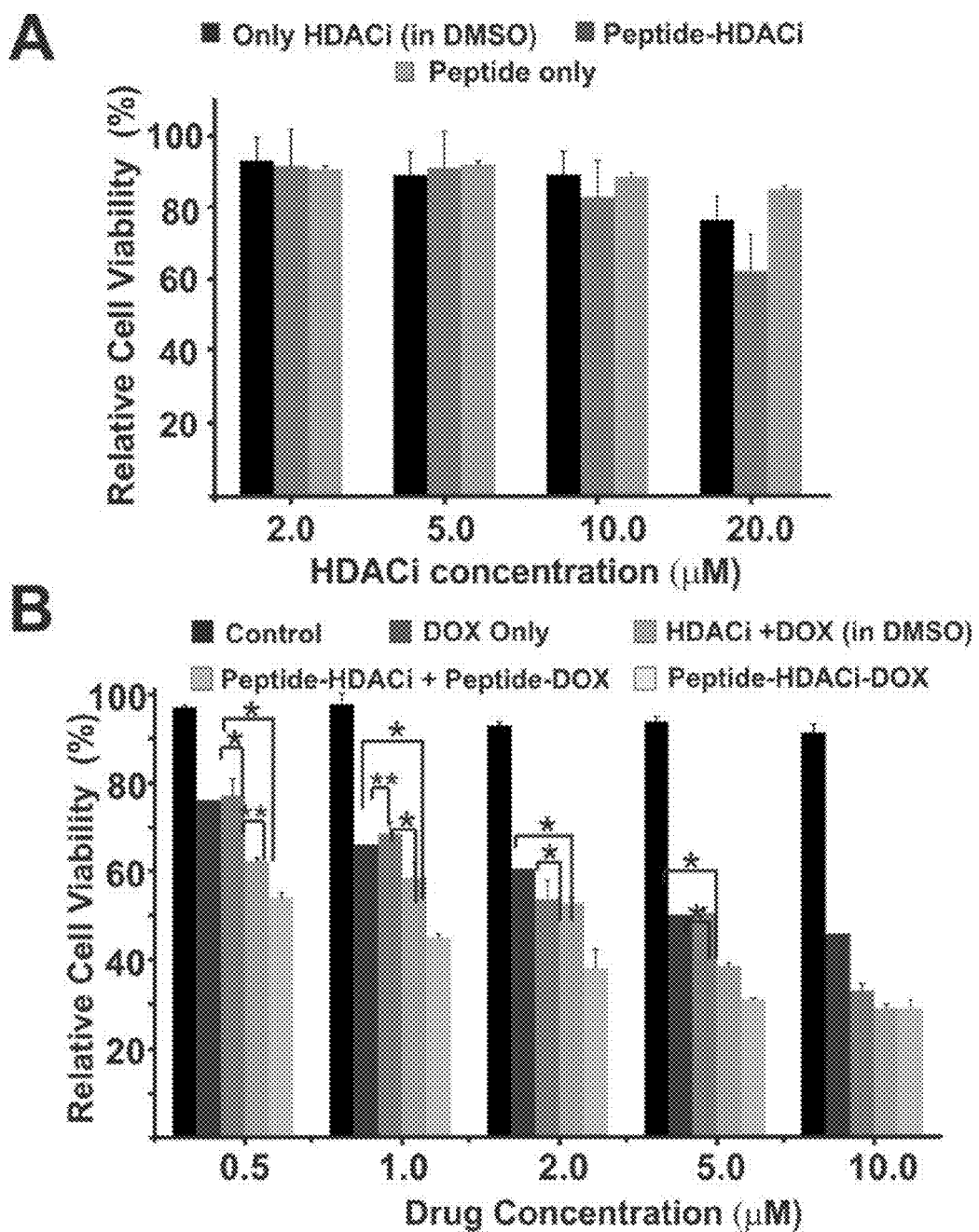
FIG. 2 shows a graph of the effect of the dendritic polypeptide-mediated co-delivery of multiple small molecule drugs (DOX and DACi) on the synergistic inhibition of brain tumor cells. (A) Comparison of cell viability of brain cancer cells by delivery of the HDACi in DMSO or conjugated to the polypeptide and (B) Synergistic inhibition of cell viability as determined using the MTS assay by co-delivery of DOX and HDACi conjugated to the same polypeptide as compared to delivery of DOX alone or combination of DOX and HDACi in DMSO or on different peptide molecules. Cell viability of untreated cells was used as control. The results are presented as means±SE from three independent experiments. Student's unpaired t-test was used for evaluating the statistical significance of the cytotoxicities (*=P<0.01, **=P<0.05).

After establishing the controlled release behavior of the inventive drug-dendritic polypeptide conjugates, their efficacy in brain tumor cells in vitro was tested. U87-EGFRvIII brain cancer cells were as a model. First the biocompatibility of the dendritic polypeptide carrier was assessed by treating the U87 cells with increasing concentrations of the dendritic polypeptide. The dendritic polypeptide was found to be highly biocompatible with greater than 95% cell viability even at higher concentrations. In order to assess the cooperative effects of the HDACi and DOX on the inhibition of brain tumor (GBM) cell proliferation, the anti-proliferative capability of the drugs (HDACi and DOX) was first assessed in U87-EGFRvIII cells using dimethyl sulfoxide (DMSO) as the solvent, FIG. 2. DOX alone was found to have an $IC_{50}$ of 5.0 μM which is consistent with previous reports. On the other hand, the synthesized HDACi was found to have no effect on the extent of cell death even at a high concentration (20 μM). However, when the HDAC inhibition capability was examined using an ELISA-based assay, it was found that the HDACi was capable of inhibiting the enzyme by ~40% even at a very low concentration of 2 μM. Hence, the results prove that HDACi would be capable of sensitizing the U87 cells to a DNA-damaging drug like DOX, thereby greatly enhancing its potency. The dendritic polypeptide-drug conjugates (polypeptide-HDACi, polypeptide-DOX and polypeptide-DOX-HDACi) were then delivered at various drug concentrations to the U87-EGFRvIII cells and compared the extent of cell death using a cell viability assay, FIG. 2B. It was found that the co-delivery of DOX and the SAHA analogue in equal concentrations using the inventive dendritic polypeptide decreased the $IC_{50}$ of DOX by 10 fold (0.5 um), thereby leading to an increased chemotherapeutic effect as compared to individual or combined drug treatments in DMSO. This is in agreement with the fact that the inventive dendritic polypeptide backbone increases the solubility of the hydrophobic drugs thereby increasing their uptake. Interestingly, the co-delivery of the drugs on the same dendritic polypeptide molecule had a greater effect (as opposed to their delivery on different peptides). Collectively, these observations support the hypothesis that the use of an HDACi allows for a more open chromatin structure which in turn enhances the efficiency of an anticancer drug targeting DNA or enzymes acting on DNA. Furthermore, it also shows that having both drugs on a single platform increases their efficacy many fold, possibly by localizing both the drugs at a single site as opposed to delivery using an admix.

Having demonstrated the potential of the inventive dendrimeric polypeptide as a carrier for multiple anticancer drugs, its ability to be used as a vehicle for the efficient delivery of siRNAs was also evaluated. The field of RNA interference (RNAi) therapeutics, wherein siRNAs or micro RNA (miRNA) are used to selectively mediate the cleavage of complementary mRNA sequences and thus regulate target gene expression, has made significant progress since the first demonstration of gene knockdown in mammalian cells. RNAi-based formulations offer significant potential as therapeutic agents to induce potent, persistent and specific silencing of a broad range of genetic targets. In combination with other modalities like small molecules and peptides, RNAi could prove to be a powerful tool to manipulate the expression of key oncogenes in cancer. However, despite its potential, therapeutic application of siRNA has been greatly hindered by the lack of methods to efficiently co-deliver them with traditional anticancer drugs for enhanced chemotherapeutic efficacy. Several non-viral vectors such as cationic lipids and dendrimers have been shown to be effective for the co-delivery of siRNA and anticancer drugs in vitro, in order to elicit a synergistic response. However, most of these platforms either tend to be extremely cytotoxic or are not biodegradable, thereby leading to undesirable changes in the cellular functions. The use of the inventive dendritic polypeptide as a siRNA delivery vehicle would not only aid in overcoming the above mentioned limitations of the traditional siRNA delivery vehicles, but would also aid in the co-delivery of drugs and siRNA in order to achieve a synergistic response towards the induction of cancer cell death. The utility of the inventive dendritic polypeptide backbone to co-deliver DOX (as a model apoptosis-inducing anticancer drug), and a siRNA (against the EGFRvIII oncogene) into the highly invasive U87-EGFRvIII brain tumor cells were also explored for an enhanced apoptotic effect. First, to investigate the cellular internalization and the intracellular release of siRNA, Cy3®-dye labeled scrambled siRNA was complexed to the dendritic polypeptide backbone and delivered it to U87-EGFRvIII cells. The uptake and extent of siRNA release was determined using fluorescence microscopy 24 hours post-transfection. It was found that the dendritic polypeptide not only complexed the siRNA effectively and translocated it across the cell membrane, but also released it efficiently in the cytoplasm as evidenced by diffused red fluorescence in the cell. It was also observed that dendritic polypeptide sequences lacking the histidine moieties (having only cysteine and lysine residues) complexed the siRNA but had a more punctate red fluorescence inside the cells, thereby indicating that the siRNA was not efficiently released from the endosome after uptake. These results prove that that the presence of multiple histidine residues in the dendritic polypeptide backbone is essential for ensuring the efficient endosomal rupture and release of cargo into the cellular cytoplasm. The utility of the inventive dendritic polypeptide for the targeted delivery of dye-labeled siRNA to the U87 cells was also demonstrated. In order to confer specificity, the targeting peptide arginyl-glycyl-aspartic acid, having a terminal cysteine residue (RGDC), was conjugated to the cysteine side chain of the inventive dendritic polypeptide backbone using a disulfide-linkage. The RGD motif is known to bind to the $\alpha_v\beta_3$ integrin receptors, which are found to be highly overexpressed on the surface of brain cancer cells and expressed in lower amounts on the HeLa cells, which in turn helps in the efficient uptake and internalization of RGD-labeled polypeptides. The dendritic polypeptide-RGD conjugate was complexed with a Cy3®dye-labeled siRNA in order to test the targeted delivery of the siRNA to brain tumor cells in comparison to HeLa cells, which are known to have low expression of the above integrin. It was found that the presence of RGD moiety on the polypeptide allowed for increasing the uptake of siRNA into U87-EGFRvIII cells as compared to HeLa cells, which is consistent with the expression levels of the integrin receptor on the respective cell lines. These results demonstrate the potential of the inventive dendritic polypeptide nanocarrier for delivering the therapeutic molecules to only the target cancer cells. The siRNA knockdown efficiency of the inventive dendritic polypeptide-siRNA complexes was then optimized at different dendritic polypeptide concentrations in U87 glioblastoma cell-lines which were genetically modified to constitutively express the enhanced green fluorescent protein (U87-EGFP). The decrease of green fluorescence intensity due to siRNA-mediated EGFP silencing was monitored using fluorescence microscopy over a time-period of 72 h to quantify the knockdown efficiency of the inventive polyplexes. A 70% decrease in the GFP intensity was observed after 72 h of siRNA treatment as compared to control cells, thus confirming the efficient siRNA-mediated gene knockdown using a dendritic polypeptide of the present invention.

Figure 3:
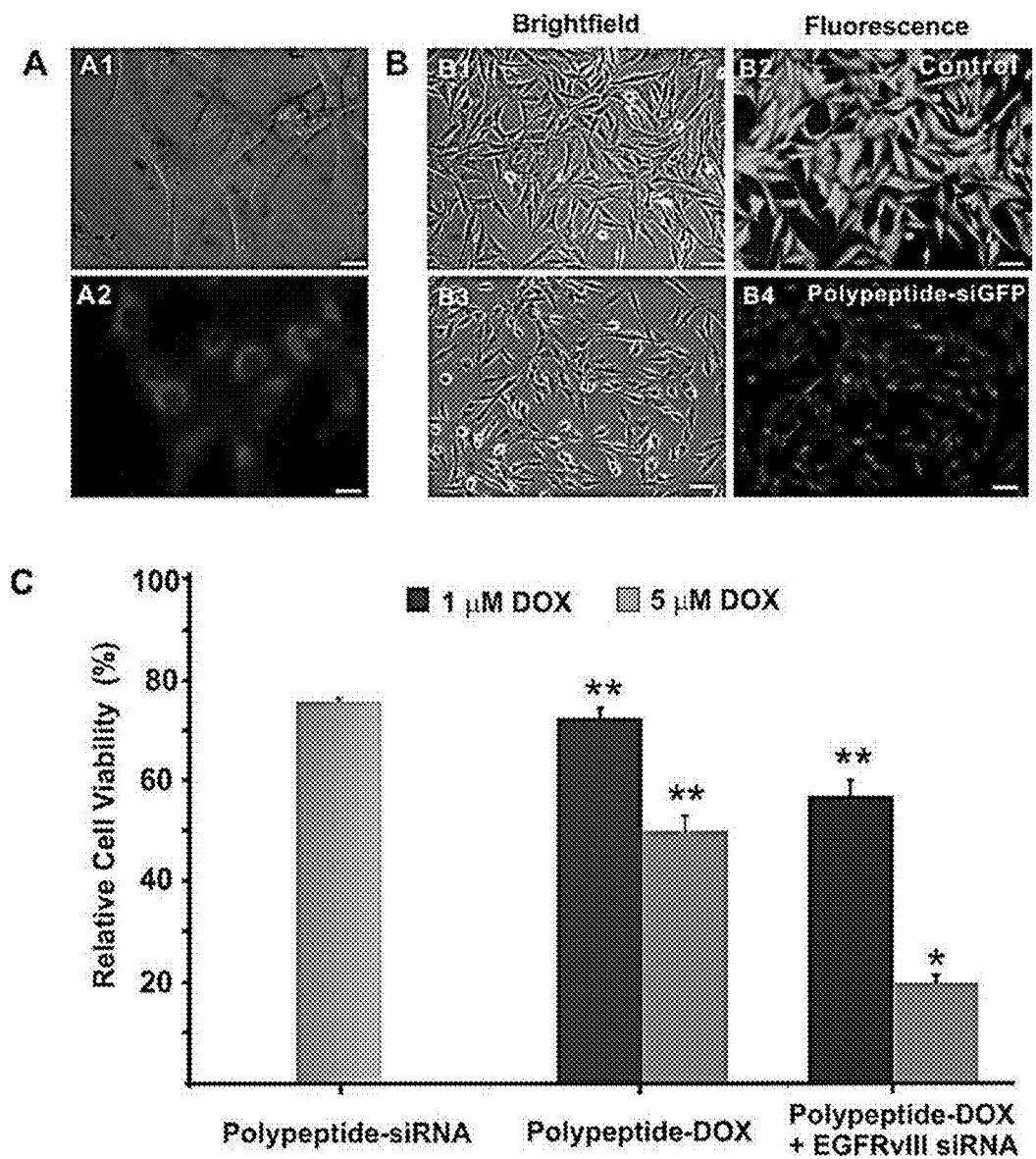
FIG. 3 shows in-vitro testing of the polypeptide-mediated uptake and release of siRNA and synergistic inhibition of brain tumor cell proliferation by codelivery of siRNA and DOX using the polypeptide nanocarrier. (A) Cellular uptake and release of the dye-labeled siRNA in U87-EGFRvIII cells as seen using fluorescence microscopy. (A1) represents the phase contrast image, and (A2) is the corresponding fluorescence image The siRNA is clearly seen in cellular cytoplasm (as evidenced by the diffused red fluorescence). (B) Silencing efficiency of the Polypetide-siGFP in stably transfected U87-EGFP glioblastoma cells (bottom) as compared to the control U87-EGFP cells (top) with polypeptide-scrambled siRNA; (B1) and (B3) represents the phase contrast image while (B2) and (B4) are the corresponding fluorescence images. Fluorescence images clearly show the knockdown of EGFP in the polypeptide-siEGFP transfected cells after 72 h. Scale bar is 50 µm. (C) Enhanced cell death by delivery of polypeptide-DOX-EGFRvIII siRNA conjugates as compared to delivery of polypeptide-DOX alone or polypeptide-EGFRvIII siRNA. The results are presented as means±SD (n=3). Student's unpaired t-test was used for evaluating the statistical significance of the cytotoxicities of the polypeptide-DOX-siRNA codelivery as compared to polypeptide-DOX or polypeptide-siRNA alone (*=P<0.01, **=P<0.05).

Having demonstrated the uptake and efficient gene silencing capability of the dendritic polypeptide-siRNA constructs, the main goal of co-delivering siRNA and DOX for targeting the oncogenic EGFRvIII-phoshphatidylinositol-3-kinase (EGFR/PI3K) signaling pathways to achieve a cooperative chemotherapeutic effect was then demonstrated. The PI3K pathway, implicated in the proliferation and apoptosis of brain tumor cells, is known to have significant crosstalk with other signaling pathways which are affected by DOX. In particular, DOX treatment and the siRNA-mediated inhibition of PI3K, are both known to significantly enhance the p53 tumor suppressor gene levels, thereby leading to a synergistic effect. To this end, DOX was co-delivered with siRNA against EGFRvIII oncogene to deactivate the target signaling pathway in a selective and efficient manner. It was found that the co-delivery of DOX and EGFRvIII siRNA led to a remarkable increase in cell death (80% cell death at 5 µM DOX and 100 nM siRNA) as compared to the delivery of DOX or siRNA alone at the same concentrations. FIG. 3 illustrates the synergistic effect of siRNA and DOX. Thus, these results demonstrate the cooperative effect on inducing the apoptosis of brain tumor cells using the right combination of siRNA and anti-cancer drugs. Collectively, the co-delivery approach using the inventive dendritic polypeptide carrier would greatly enhance the therapeutic effects of different modalities, thereby reducing the dose of anticancer drugs, mitigating their toxic side-effects and effectively circumventing drug-resistance in cancers.

In summary, a novel dendritic polypeptide-based drug delivery system has now been developed which is capable of delivering multiple anti-cancer therapeutics to brain tumor cells. It was found that the dendritic polypeptide backbone allows for high drug loading and the subsequent controlled release of drugs over time using multiple physiological stimuli such as pH and redox environment. The combined delivery of HDACi and DOX using the dendritic polypeptide-based system led to a remarkable increase in cell death as compared to the individual treatments. In particular, a 10-fold decrease in the $IC_{50}$ of DOX was achieved using this approach, thus demonstrating the utility of the inventive dendritic polypeptide system for enhancing conventional therapies. Furthermore, the dendritic polypeptide was also shown to effectively condense and deliver siRNA to the tumor cells, thereby demonstrating the potential for the co-delivery of complementary therapeutic modalities. This strategy of co-delivering multiple anti-cancer drugs with therapeutic siRNA is particularly advantageous for in vivo applications, so that both the moieties are delivered to the target cells using a single delivery platform, thereby precluding the necessity for multiple injections. The results also proved that the co-delivery system can not only efficiently deliver the siRNA simultaneously with DOX into cytoplasm, the thus-delivered siRNA can also be efficiently released and effectively silence the targeted oncogenes to obtain a synergistic response. Collectively, these results open up new avenues for chemotherapy by reducing the dose of anticancer drugs required, mitigating their toxic side-effects and effectively circumventing drug resistance in difficult to treat malignancies such as brain and breast tumors.

The invention claimed is:

1. A dendritic polypeptide nanocarrier, having a formula:

[(Histidine)$_l$(Lysine)$_m$(Cysteine)$_n$-L]$_p$-X, wherein l, m, and n are each an integer independently selected from 3, 4, 5, 6, 7, 8, 9, and 10;
p is an integer selected from 3, 4, and 5;
X is N, P or C; and
L is a spacer.

2. The dendritic polypeptide nanocarrier of claim 1, wherein the core atom is nitrogen and the spacer is an optionally substituted $C_{2-8}$ alkyl.

3. The dendritic polypeptide nanocarrier of claim 1, wherein
l and n are each 3;
m is 7;
p is 3; and
X is N.

4. A conjugate comprising the polypeptide dendritic nanocarrier of claim 1 and an agent selected from the group consisting of drug, targeting agent, small RNA, sensitizing agent, and diagnostic agent.

5. The conjugate of claim 4, wherein the agent is an anticancer drug selected from the group consisting of taxol, erlotinib, camptothecin, carboplatin, doxorubicin (DOX), paclitaxel, gefitinib and bleomycin.

6. The conjugate of claim 5, wherein the anticancer drug is Doxorubicin (DOX).

7. The conjugate of claim 5, further comprising a sensitizing agent or a second anticancer drug.

8. The conjugate of claim 7, wherein the sensitizing agent or the second anticancer drug is a histone deacetylase (HDAC) inhibitor or a histone acetyltransferase (HAT) activator.

9. The conjugate of claim 8, wherein the HDAC inhibitor is suberoylanilide hydroxamic acid (SAHA).

10. The conjugate of claim 5, further comprising a small RNA.

11. The conjugate of claim 10, wherein said small RNA is siRNA.

12. The conjugate of claim 4, further comprising a targeting agent.

13. The conjugate of claim 4, wherein said agent is a small RNA.

14. The conjugate of claim 13, wherein said small RNA is siRNA.

15. The conjugate of claim 13, further comprising a targeting agent.

16. A pharmaceutical composition comprising the conjugate of claim 4 and an inert carrier.

17. A method of delivering an agent to a target cell, comprising conjugating said agent with the dendritic polypeptide nanocarrier of claim 1.

18. A method of treating a disease comprising administering to a subject in need thereof a therapeutically effective amount of the pharmaceutical composition of claim 16, wherein said disease is cancer.

19. A method of diagnosing a disease in a mammal, comprising administering the pharmaceutical composition of claim 16, wherein the conjugate provides an effective amount of an agent to diagnose the disease wherein said agent is a diagnostic agent and the disease is cancer.

20. The method of claim 19, wherein the conjugate further comprises an antibody or an antibody fragment.

21. The method of claim 19, wherein the mammal is human.

22. The method of claim 18, wherein the conjugate further comprises and antibody or antibody fragment.

* * * * *